United States Patent [19]

Maliyakal et al.

[11] Patent Number: 5,474,925
[45] Date of Patent: Dec. 12, 1995

[54] IMMOBILIZED PROTEINS IN COTTON FIBER

[75] Inventors: John Maliyakal; Kenneth A. Barton, both of Middleton, Wis.

[73] Assignee: Agracetus, Inc., Middleton, Wis.

[21] Appl. No.: 217,327

[22] Filed: Mar. 23, 1994

Related U.S. Application Data

[63] Continuation-in-part of Ser. No. 812,233, Dec. 19, 1991, abandoned.

[51] Int. Cl.⁶ .......................... C12N 15/00; C12N 15/52; C12N 5/14; C12P 21/04
[52] U.S. Cl. .................... 435/172.3; 435/69.1; 435/70.1; 435/183; 47/58; 536/24.1
[58] Field of Search .................... 435/183, 172.3, 435/70.1, 69.1, 240.4, 240.49, 52, 60, 64; 800/205, DIG. 27; 47/58; 536/24.1

[56] References Cited

U.S. PATENT DOCUMENTS 4,013,514  3/1977  Wildi .......................................... 195/68

OTHER PUBLICATIONS

Finer et al (Mar. 1990) Plant Cell Reports 8:586–589.
Lee (1980) in "Hybridization of Crop Plants" (Fehr and Hadby, eds) ASA–CSSA publ, pp. 313–325.
Joseffson, L-G (1987) J. Biol Chem 262(25):12196–12201.
Crouch et al (1983) J Mol. Appl. Genet. 2:273–282.

*Primary Examiner*—David T. Fox
*Assistant Examiner*—Elizabeth F. McElwain
*Attorney, Agent, or Firm*—Quarles & Brady

[57] ABSTRACT

Transgenic cotton plants have been created which expressed an immobilized protein in the cotton fiber cells. The cotton fiber can be recovered from such transgenic cotton plants and then used as a substrate for fixing immobilized protein for use in industrial or laboratory processes. Using an enzyme expressed inside cotton fiber, it is possible to fabricate a convenient reaction column by simply packing the cotton fiber carrying the enzyme into a column and passing substrate therethrough.

5 Claims, 9 Drawing Sheets

H6 Gene

Plasmid pSKSIH6-4RI

IMMOBILIZED PROTEINS IN COTTON FIBER

CROSS-REFERENCE TO RELATED APPLICATION

This application is a continuation-in-part of application Ser. No. 07/812,233 filed Dec. 19, 1991, now abandoned.

FIELD OF THE INVENTION

The present invention relates to the general field of the genetic engineering of plants and plant products and relates, in particular, to the production of immobilized proteins, particularly enzymes and binding proteins, in the fiber of cotton plants so that such proteins in immobilized form can be readily manufactured for use in industrial processes.

BACKGROUND OF THE INVENTION

Within the general field of genetic engineering, it has become demonstrated in recent years that it is possible to insert foreign genetic constructions into the inheritable genetic material of higher plants. Through proper manipulation of the genetic construction which is inserted into the plant, it is possible to cause the expression in the cells of plants of heterologous proteins, which then may confer upon the plant new traits which the plant species does not natively possess. Most of the activity in plant genetic engineering to date has focused on improvements to the agronomic or agricultural value of the plants, such as inserting traits for insect resistance, herbicide resistance or traits which might alter one or more of the growing characteristics of the plant. As the genetic engineering of plants becomes more refined, it also now becomes possible to engineer specific plants so that the products produced by the plant have novel and desirable characteristics. The concept described here is directed toward such a novel industrial application for a product produced by cotton or other fiber producing plant.

Cotton was one of the first economically important field crops which was genetically engineered. U.S. Pat. No. 5,004,863 describes what is believed to be the first successful genetic engineering of cotton plants and lines. The transformation technique described in that patent was based on the use of an Agrobacterium, a plant pathogenic bacteria which has an inherent capability to transfer some of its genetic material into plant cells. The same research was reported by Umbeck et al., *Bio/Technology*, 5:263–266 (1987). Another, newer technique for introducing genes into plants has proven to have wide applicability, due to its ability to transfer genes into plant cells independent of a biological vector such as Agrobacterium. This method is based on the acceleration of small carrier particles carrying genes coated on them into susceptible plant tissues. U.S. Pat. No. 5,015,580 describes an apparatus and method for transforming soybean plants which makes use of an accelerated particle genetic transformation technique.

There are many applications in industry, research, and laboratories where it is desired that a protein be immobilized onto a solid matrix. See, for example, Cowan, D. A., in *Biotechnology/The Science and Business*. V. Moses and R. E. Cape Eds. 1991, pp. 311–340. Often it is desired to immobilize an enzyme to a solid matrix in such a fashion that its catalytic ability is not affected. One example of such an immobilized enzyme of industrial use is glucose isomerase, which is widely used for the production of fructose syrups in the food industry. The immobilization of enzymes offers several advantages over similar systems in which the enzyme is not immobilized. Systems based on enzyme immobilization offer better protection against denaturing or degradation of the enzyme, typically offer better yields, and are more amenable to efficient reactor technology design, due to the flow-through nature of the reaction. In the past, if an enzyme was immobilized, it was typically fixed or bonded on a solid substrate or matrix. Some of the commonly used enzyme substrates include cellulose, cellulose acetate, silica gel, stainless steel coated with titanium dioxide, polyacrylamide, porous glass, metal oxides, and agarose.

In general, there have been two approaches to the immobilization of useful proteins, a physical approach and a chemical approach. In the physical mode of immobilization, the enzyme or protein is absorbed or entrapped in a matrix. In the chemical mode of immobilization, a variety of chemical processes are utilized to form covalent attachment, or strong cross-linking, between the enzyme and the matrix to which it is attached. The physical method of immobilization, in which the protein is entrapped or absorbed, have a weakness in that it may be susceptible to leakage. On the other hand, chemical immobilization is often relatively laborious, and some of the chemical agents used for the immobilization, notably thiophosgene, are extremely toxic. No system of biological immobilization of useful proteins for industrial procedures has heretofore been reported.

Another disadvantage of currently available techniques for producing immobilized proteins is that the protein must be produced separately and thus somehow entrapped or linked to the substrate. These and other relevant topics on enzyme immobilization and industrial enzymology are reviewed in Godfrey, T. and Reichet, J. Eds. 1983; *Handbook of Enzyme Biotechnology*, Wiseman, A. Ed. 1985. No system presently existing is capable of producing both a matrix and the immobilized protein in a single production process.

SUMMARY OF THE INVENTION

The present invention is summarized in that a transgenic cotton plant is provided which will produce cotton fiber having an immobilized foreign protein of utility in an industrial process.

It is an object of the present invention to provide a novel product from transgenic cotton, i.e. cotton fiber imbued with a trait of production of a protein useful for an industrial process, the protein being inherently immobilized in the cotton fiber.

It is an advantage of the present invention that it facilitates the production of immobilized proteins on a support by the creation of transgenic cotton plants which will inherently produce in their fiber the immobilized protein which is already attached to a suitable support, the support being the cotton fiber itself.

It is another advantage of the present invention in that once a transgenic cotton producing the immobilized protein in its fiber is created, the production of large quantities of immobilized protein in fiber is thereafter rendered inexpensive, since the material can be created through normal agricultural cultivation of the cotton plants themselves and harvesting of the resulting fiber.

Other objects, advantages, and features of the present invention will become apparent from the following specification when taken in conjunction with the accompany drawings.

DETAILED DESCRIPTION OF THE INVENTION

Figure 1:
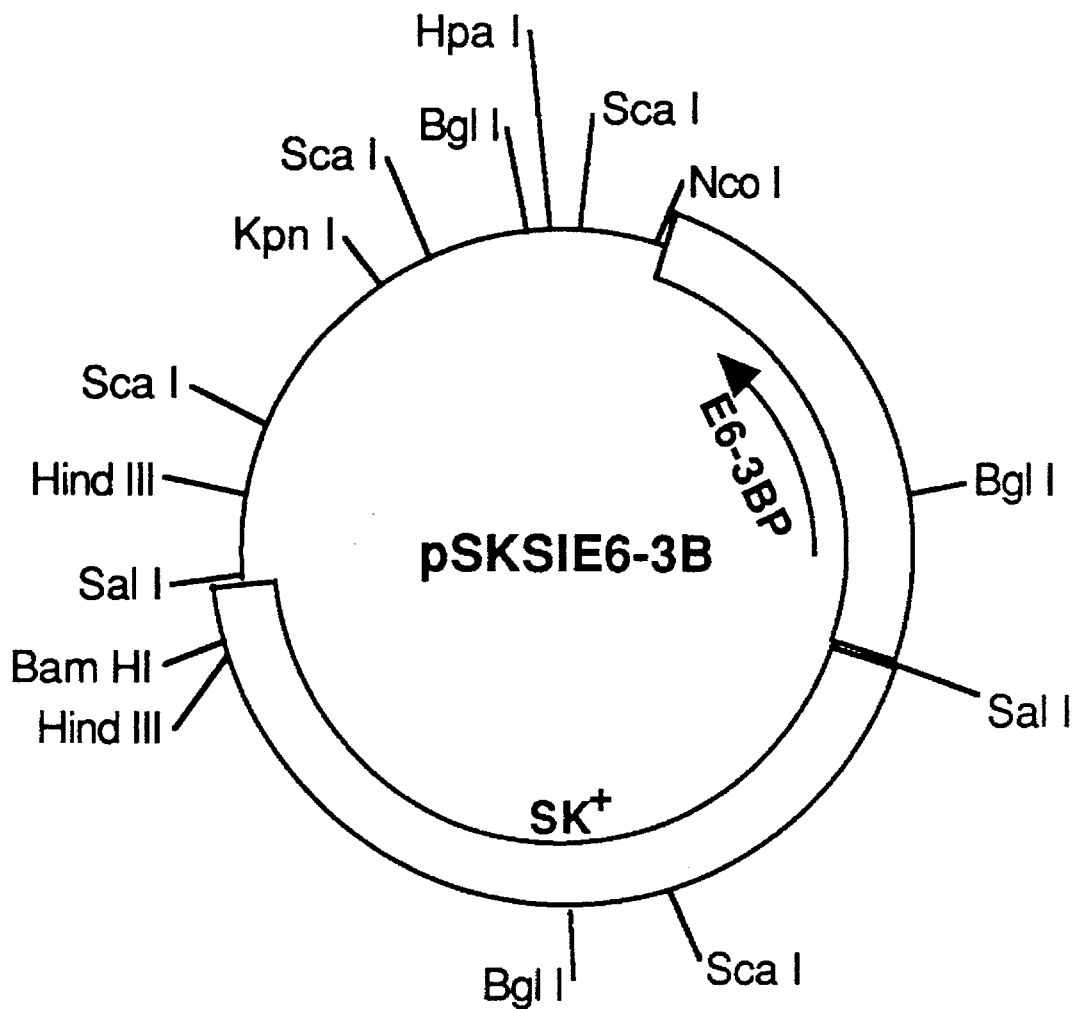
FIG. 1 is a schematic illustration of the subclone of the E6 promoter.

The present invention is directed toward the creation of transgenic cotton plants, or plants of other fiber producing species, which has a protein of industrial interest produced in the fiber produced by the plant. The gene coding for the expression of the protein is incorporated into the genome of the cotton plant such that the cotton plant will produce the protein in one or more of its tissues. Preferably, the expression characteristic of the gene inserted into the plant is designed such that the protein will be expressed preferentially or exclusively in the fiber cells of the cotton plant. The gene coding for the protein can be unaltered so that the protein is simply produced in the cotton fiber cells, or the gene may also be modified so as to include a coding sequence for an anchoring peptide which will anchor the protein in the cell wall, or the membrane of the cotton fiber cell, and there anchor the protein in that membrane. Once such a transgenic plant is produced, through a process such as that described below, it then becomes possible to produce large quantities of cotton fiber containing the immobilized protein in a fashion much more convenient than could be achieved by conventional protein immobilization techniques. One can simply grow the cotton plants and harvest the resulting cotton fibers. The cotton fibers produced by such transgenic plants would inherently have the immobilized protein in their fiber.

It is an advantage of immobilizing proteins in cotton fiber that the cotton cell wall is permeable to a large number of molecules. Thus, as shown in the example below, it is possible simply to have an active protein, such as an enzyme, entrapped inside the lumen of a cotton fiber and the substrates upon which the enzyme acts can readily permeate through the cell wall to be catalyzed by the enzyme. In addition, the accessibility of the substrates to the enzyme can be increased by mechanically breaking the cotton fiber into smaller pieces either by mechanical, chemical, or thermal means. Any of these methods would provide additional access for the substrate to the enzyme. If the cotton fibers are to be broken, then it would be preferred that the protein within the cotton fiber be anchored to the cell wall, so that it is structurally immobilized. However, anchoring the protein to the cell wall may not be required, even if the cotton fibers are broken, due to the physical shape of the cotton fiber. The cotton fiber is an elongated cell which can be modeled as a long closed-end tube. An enzyme will tend to remain within the cell during substrate interaction, and reaction kinetics are more likely to favor diffusion of the substrates, or the reaction products, out of the cotton fiber interior than migration of the enzyme itself.

The invention here is intended to describe a widely applicable methodology to immobilize a variety of proteins in a cellulose matrix consisting of cotton fibers. The cotton fiber itself is a single epidermal cell created by the cotton plant. The fiber cell contains primary and secondary cell walls, a thin layer of cytoplasm, a surrounding plasmalemma, and an enormous vacuole. Thus, again on a simplified level, the cotton fiber can be considered as an elongated cellulose tube closed at both ends. During the development of the fiber, the cell wall components are synthesized and transported to the developing cell wall by a functionally integrated membrane system of endoplasmic reticulum, Golgi complex and plasmalemma. In normal fiber cell development, newly synthesized cell wall polypeptides are released into the endoplasmic reticulum lumen from which they are transported for incorporation into the developing cell walls. Many hundreds of genes, and corresponding proteins, are required for the development and maintenance of a single cotton fiber cell. Some of these proteins are unique to the cotton fiber cell and are not expressed in other cell types. Other of these proteins are common to other cell types within the cotton plant. It has been demonstrated here that the incorporation of other proteins into this developmental process within the cell and does not disrupt the formulation and development of normal-appearing cotton fiber. Further it has been found that a foreign protein can be readily incorporated into the cotton fiber, without sacrificing the enzymatic activity of the protein.

It is preferred that the gene construction coding for the expression of the foreign protein in the cotton fiber be a tissue specific gene construction. In other words, it is preferred that the protein be expressed preferentially or solely in the cotton fiber cell, and not in other portions of the cotton plant. It has been an objective of some of the research described below to identify fiber specific genes and their regulatory elements, in order to serve a number of purposes related to this invention. First, it is understood that the promoters of fiber specific genes can be utilized to express foreign protein preferentially in fiber tissues, and not in other tissues of the cotton plant. Secondly, by identifying a set of fiber specific genes and by characterizing their function within the developing cotton fiber itself, it is possible to identify regions of cell wall proteins that are anchored in the cell walls of the cotton fiber. Such cell wall anchoring regions can readily be utilized to anchor other foreign proteins to the cell walls of cotton fibers, even if the proteins do not normally have an ability for being anchored in such fashion.

It is envisioned that proteins of several classes can be utilized within the process of the present invention. One attractive type of protein for use within this invention is enzymes. A number of enzymes used in industry are currently immobilized as used in industrial processes, and which catalyze reactions which are conducted at temperatures and conditions which would not be destructive to cotton fibers. Examples of such enzymes include amylases, glucoamylases and glucose isomerase, which are used in the food processing industry to convert starch to sweetening agents and for the production of other organic materials from starch compounds. Another useful class of enzymes are proteinases, which are used for the hydrolysis of high molecular weight proteins and which are used in detergents, in leather manufacture, in the food industry, and in the manufacture of alcoholic beverages. Enzymes known as pectinesterases, and several related enzymes, are used for pectin hydrolysis in the food industry. A class of enzymes known as lipases are used for the cleavage of ester linkages in triglycerides, and are used both in the food industry and for effluent treatment. The enzyme beta-galactosidase is used industrially for the hydrolysis of whey lactose. An enzyme known as thermolysin is used in the production of the artificial sweetener aspartame. An enzyme known as sulphydryl oxidase is used in the reduction of the cooked flavor of milk. Enzymes known as catalases are used to remove hydrogen peroxides from milk, cheese, and egg processing, and are used in the sterilization and oxidation of plastics and rubbers. Many of these enzymes have been cloned, and the DNA sequences for these enzymes are readily available. The genes for others of these enzymes can be cloned using conventional cloning techniques, or the polymerase chain reaction, and can then be joined to fiber specific promoters and membrane anchoring sequences to construct foreign genetic constructs for use in the present invention.

Other proteins, in addition to enzymes, can be advantageously immobilized in cotton fiber. A significant class of such proteins are those which have affinities to other compounds, so that the proteins can be used for separations or other absorptive applications. For example, bacteria, fungi, plants and animals all contain large numbers of proteins that have specific interactions with agents such as metal ions and toxic compounds, and have high affinities for those agents. A class of proteins known as metalloproteins contain prosthetic groups that bind specifically to metal ions. An example of such a prosthetic group is the porphyrin group in hemoglobin. Some other examples of metal ion binding proteins include parvalbumin, which binds to calcium, and metallothionein, an animal protein that binds large amounts of metal ions, especially zinc. Bioimmobilized absorptive proteins in cotton fiber would thus be useful for separation processes, or to scavenge selective metal ions from a reactant stream, which might be present in the environment or in the output of an industrial process. Such absorptive proteins could also be used for purifications in industrial processes.

It is also envisioned that streams of flowing material could be degraded by microbial enzymes. It is known that certain pollutants, whether natural or synthetic, and certain pesticides and other durable organic compounds in the environment, can be degraded by microbial enzymes. The sequencing of such enzymes, and the cloning of DNA sequences coding for those enzymes, has become a widely utilized technology. The incorporation of coding sequences for such enzymes into the cotton fiber cells will produce proteins having potentially higher stability, due to the fact that the enzymes will be protected from denaturants. It is known that some microorganisms, for example *Pseudomonas putida*, possessed dehalogenases that are capable of degrading certain pesticides and herbicides, and rendering them less toxic. Similarly, hydrolysis of organophosphate insecticides have been observed by microbial enzymes. Certain lignolytic fungi, such as *Phanerochete chrysosporium* and *Coriolus versicolor*, contained enzymes that decolorized chlorinated lignin derivatives produced by paper pulp mills. Chemical bleaching of the lignin, and the resulting environment damage, could be minimized or treated by using cotton fiber filtrates containing the appropriate lignin degrading enzymes. Microorganisms that degrade organophosphate pesticides such as parathion have also been isolated and characterized. Parathion and other such pesticides have been used extensively worldwide. Their use has been severely restricted in the U.S. because they are potent inhibitors of acetylcholinesterase, have low $LD_{50}$ valves, and pose groundwater contamination problems.

The use of pesticide-degrading bacteria in a bioremediation plan requires well-defined growth conditions and raises public concerns over release of genetically engineered organisms. In contrast, by stably immobilizing active pesticide-degrading enzymes, such as the model enzyme parathion hydrolase in cotton fibers such fibers may be integrated into an effective bioremediation strategy that overcomes the real and perceived limitations of bacterial bioremediation. Other examples of useful immobilized enzymes would include the removal of nitrates, the degradation of phenols from the waste of hospitals, laboratories, and industrial processes.

It is also possible to immobilize antibodies within cotton fiber. The antibodies could be monoclonal or polyclonal. Antibodies are proteins which have specific affinities to specific compounds, referred to as antigens. Cotton fiber having immobilized antibodies could be used in diagnostics, or to bind chemical reagents for their purification or removal. A large number of current separation or purification techniques are based on the use of immobilized monoclonal antibodies, prepared against the antigen which is sought to be purified. Cotton fiber would provide a suitable substrate for the use of such immobilized monoclonal antibodies in industrial, laboratory, or research purification processes.

Another function for which proteins could be immobilized in cotton fibers would be for medical applications, such as wound dressings. Cotton fibers are often incorporated into dressings used in medicine to treat wounds. It would be possible to incorporated into the cotton fiber, and immobilize within the cotton fiber, protein antibiotics or therapeutic proteins which might assist in the healing process. For example, certain wound healing peptides, or growth factors, might be incorporated into cotton fiber, and immobilized within it. Such cotton fiber incorporated into a wound dressing might facilitate healing, due to the interaction of the protein with the tissues below.

In order for plants and fiber in accordance with the present invention to be utilized, there are two essential capabilities and one preferred capability which must be developed. The two essential capabilities are the ability to construct a foreign gene coding for the protein sought be incorporated within the cotton fiber and the ability to transform cotton plants so as to insert therein the foreign gene. The preferred capability is the use of a promoter sequence capable of conditioning tissue specific expression of a foreign protein either preferentially or solely in cotton fiber cells.

The first essential capability is the construction of a gene coding for the foreign protein sought to be immobilized in the cotton fiber. Described above are various enzymes, and other proteins, which can be utilized within the present invention. Genes for the proteins can be isolated using presently available techniques of molecular biology and, in fact, many of the genes are readily available for commercial proteins of interest. It has previously been demonstrated that the expression of heterologous proteins in plants is not difficult, if appropriate promoter sequences are available.

Proteins can be expressed in cotton fiber cells using either a tissue specific promoter or a constitutive promoter, which would express the protein throughout the tissues of the cotton plant. The techniques for constructing genes for the expression of foreign genes in plant cells are well known. Genetic constructions for expressing foreign proteins in plants typically include a promoter sequence effective in plants, a transcriptional or translational enhancer sequence located between the promoter and the coding sequence, a coding sequence for foreign protein, and a downstream transcriptional terminator, or polyadenylation sequence, capable of ending the transcription in plant cells in vivo. The sequences other than the protein coding sequence are referred to as regulatory sequences and the regulatory sequences flank the protein coding sequence, both preceding and following it. The promoter may also include one or more control elements to cause more sophisticated regulation of gene expression. Suitable transcriptional or translational enhancers include 5' noncoding sequences from abundantly expressed viral genes. Several examples of such enhancers are known in the art and available to those of ordinary skill.

The ability to transform cotton plants with foreign gene constructions is now well accepted in the field of plant genetic engineering. One method for transforming genes into cotton plants is described in U.S. Pat. No. 5,004,863, which describes the Agrobacterium-mediated transformation of cotton plants. Through that technique, genes can be inserted into the germ line of cotton plants, which can then be cross-bred with other cotton varieties to transfer the inserted gene into any desired genetic background. As an alternative, a recently developed technique permits the direct insertion of foreign genetic constructions directly into cotton plants of virtually any genetic background. This technique, described in further detail below, makes use of an accelerated particle process of plant transformation. The use of an accelerated particle plant transformation system has previously been demonstrated to be useful in soybean, as described in U.S. Pat. No. 5,015,580, which describes an apparatus which may be used for the process of transforming cotton as well. By whatever method is used to transform an original cotton plant, however, the performance and utility of the transgenic cotton plants, and the resulting fiber produced from them, is independent of the method of transformation. Once the gene is stably inserted into the germ line of a cotton plant, it is thereafter inheritable by normal Mendelian inheritance, and may be passed on to any progeny of the original transgenic plant. Suitable crossbreeding can transfer that inheritable trait into any desired genetic background. Thus, once the initial transgenic cotton plant has been created which expresses the desired protein into cotton fiber, the trait can readily be transferred to any desired cotton plant with which the original plant can be cross-bred. Since the advent of particle-mediated transformation allows genes to be directly inserted into any genetic background, this makes the total spectrum of cotton germ plasm available for creating transgenic cotton in accordance with the present invention.

It is thus preferred within the present invention that the gene coding for the protein to be expressed in cotton fiber be located in the genetic construction downstream from a tissue specific promoter which conditions expression of the protein preferentially in cotton fiber. Set forth in Sequence ID 1 and Sequence ID 2 below are two such tissue-specific promoters, designated E6 and H6, which have been found to preferentially express proteins in cotton fiber. These promoters are made available through the sequences ID 1 and ID 2 below. The promoters can be reconstructed by oligonucleotide synthesis and assembly, or the sequences can be used to create probes for re-isolating the promoter sequences from genomic Sea Island cotton DNA. The present invention can also be implemented through the use of a constitutive promoter, which expresses in all the cells of the cotton plant, such as the widely used cauliflower mosaic virus 35S promoter described in one of the examples below. However, it would be preferable to achieve tissue-specific promoter activity, so as not to affect the remaining portions of the cotton plant to minimize any potentially undesirable change in the morphology or developmental characteristics of the plant. In addition to the fiber specific promoters described here, it is also possible to isolate other fiber specific promoters. The methodology for doing so will become apparent from several of the following examples, which describe how the tissue specific promoters described here were isolated. In brief, a cDNA library can be created from cotton fiber cells, and then the library can be screened against cDNAs obtained from other tissue types of the cotton plant, to therefore identify those cDNAs which express preferentially in cotton fiber cells. Using the cDNA clones, genomic clones can be recovered, and the DNA sequences upstream from the coding sequences can be analyzed to determine regions having effective promoter activity. The promoters which are obtained, such as the one described below, may include excess DNA in addition to that strictly essential for promoter activity, but excess DNA is not a problem, as long as effective promoter activity is obtained.

It is further intended that an alternative of the present invention uses an anchoring sequence attached to the protein of interest to be immobilized in cotton fiber cells. As used here, an anchoring sequence refers to an amino acid sequence that causes the protein of which it is a part to be bound to or integrated in the cell wall of the cotton fiber. Two strategies are apparent for achieving this anchoring. One strategy is based on integrating into the protein to be expressed an anchoring sequence to integrate the protein into the fiber plasma membrane. A second strategy is based on sequences having binding affinity to cellulose.

For the first approach, there are a number of eukaryotic N-terminal topogenic sequences that target peptides to specific compartments in cells. For example, it is well-known that signal peptides serve the function of translocation of produced protein across the endoplasmic reticulum membrane. Similarly, transmembrane segments halt translocation and provide anchoring of the protein to the plasma membrane. Johnson, K. D. et al., *The Plant Cell*, 2, 525–532 (1990); Sauer, N. et al. *EMBO J.*, 9, 3045–3050 (1990); Mueckler, M. et al., *Science*, 229, 941–945 (1985). Mitochondrial, nuclear, chloroplast, or vacuolar signals target expressed protein correctly into the corresponding organelle through the secretory pathway. Von Heijne, Cr., *Eur. J. Biochem.* 133, 17–21 (1983); Yon Heijne, Cr., *J. Mol. Biol.* 189, 239–242 (1986); Iturriaga, Cr. et al., *The Plant Cell* 1, 381–390 (1989); McKnight, T. D., et al., *Nucl. Acid Res.* 18, 4939 (1990); Matsuoka, K. and Nakamura, K., *Proc. Natl. Acad. Sci. USA* 88, 834–838 (1991). For the purposes of the present invention, the most appropriate signal would be a transmembrane segment or anchor region. Such an anchor region would anchor a protein to the membrane by its amino-terminus portion, thereby exposing most of the mass of the protein to the cytosolic face of the membrane. Alternatively, the amino-terminus of the protein can remain anchored, while the rest of the protein is exported across the membrane. There are also carboxyl-terminus anchor sequences that hold proteins in place. The amino-terminal sequences of some fiber specific proteins have been identified that have similarities to transmembrane segments. One such sequence for a cotton fiber protein designated H6 is presented in SEQ. ID. NO. 3 below. Amino acids 1 through 25 of the H6 sequence in SEQ. ID. NO. 3 have general characteristics of a signal peptide. Moreover, it had been demonstrated that bacterial signal peptides may function correctly in plants. (Herrera-Estrella, A. et al., *Proc. Natl. Acad. Sci. USA* 9534–9537 (1990). Hence, many of the known amino-terminal or carboxyl-terminal transmembrane segments may also be useful to anchor proteins in the fiber cells of cotton plants. It is anticipated that DNA corresponding to the transmembrane segments of such peptides may be isolated by polymerase chain reaction. Saiki et al., *Science*, 239 pp. 487–491 (1988). Appropriate primers containing restriction sites may be used to amplify the DNA segments from the genomic DNA of plant, bacteria, or yeast hosts. The inclusion of restriction sites in the primers will allow that the amplified DNA, after purification, to be digested with appropriate restriction enzymes, so that the transmembrane coding segments can be readily cloned into appropriate plant expression vectors.

The second strategy to bind the protein to the fiber cell wall is based on cellulose binding domains can be used to create fusion protein which will deposit the protein within the thick secondary cell wall. A number of microbial enzymes degrade cellulose and hemicellulose of plant cell walls. For example, endo-β-1, 4-glucanase, exo-β-1, 4-glucanase, and β-glucosidase degrade cellulose while xylan, the major constituent of hemicellulose, is hydrolysed by β-1-4 xylanase and β-xylosidase. Analysis of these cellulases have shown that they typically have two distinct functional domains, a catalytic domain and a cellulose binding domain. The cellulose binding domain is typically not required for catalytic function, but may simply serve to position the enzyme on its substrate. It had been shown that the fusion of a cellulose binding domain to heterologous proteins results in hybrid proteins that are able to bind to cellulose. Greenwood, J. M., *FEBS Letters*, 244:127–131 (1989), Ong. E. et al., *Bio/Technology*, 7:604–607 (1989). In those procedures, the hybrid proteins were produced in bacteria, purified, and then bound to cotton fiber. Here, it is suggested that the coding region for the cellulose binding domain be incorporated into the coding region for the heterologous protein in the plant expression cassette inserted into the cotton plant. A signal peptide directing transport to the cell wall may also be included, so that the protein is both directed toward then bound to the fiber cell wall. The bound protein will then remain with the fiber cell wall if fiber lysis occurs. A nucleotide sequence for a suitable cellulose binding domain from a cellulose enzyme (xylanase) is set forth in SEQ. ID. NO. 4 below, and is repeated from Kellet et al., *Biochem. J.*, 272:369:376 (1991). The cellulose binding domain has been identified to include the first 100 amino acids encoded by this sequence from its amino terminus.

A modification of this second approach is to use integral cell wall proteins to direct proteins/enzymes into cell walls. An example is extensin, a hydroxyproline rich glycoprotein found in the cell walls of dicotyledonous plants (Lamport, D. T. and Catt, J. W. 1981 in *Plant Carbohydrates II: Encyclopedia of Plant Physiology*, New Series 13B, Tanner, W. A. & Loewus, F. A. eds. pp. 133–165.) DNA sequences of a number of extensins are known (Chen, J. and Varner, J. E. 1985, *EMBO* 4, 2145– 2151). If one were to use extensin to transport an enzyme or protein into the cellulose wall, then the fiber could be opened up and the endogenous enzymes and proteins could be washed out, leaving only the cellulose wall together with the bound enzyme/protein. This preparation would have the advantage of being much purer, since a number of unneeded proteins would have been removed. The sequence of a carrot extensin gene is given in SEQ. ID. NO. 5 below and is from Chen and Varner (supra). The sequence also includes a signal peptide located from nucleotide 751 to 848 of SEQ. ID. NO. 5 below. A DNA coding sequence for such an extensin sequence can be joined to the DNA coding sequence for the protein to be immobilized, to create a fusion protein likely to be incorporated into the fiber cell wall in such a manner that the protein is physically bound to the fiber cell wall, even if the fiber itself is disrupted and its cytoplasm lost. We have also identified extensin like proteins that are integral part of the secondary cell wall of cotton fiber. One such sequence for a cotton fiber protein designated H6 is presented in SEQ. ID. NO. 3 below. The sequence is that of a full length cDNA clone. The protein corresponding to H6 has been localized to cotton fiber walls by electron microscopical studies of H6 antibody binding. A fusion protein of H6 and an enzyme is also expected to be localized within the secondary walls of fiber.

Once transgenic cotton plants expressing the immobilized protein in the cotton fiber are created, the design and fabrication of a suitable bioreactor within which to utilize the immobilized protein becomes something that can be easily accomplished. Kennedy, J. F. in *Handbook of Enzyme Biotechnology* 1985 pp. 147–201; Cowan, D. A. in *Biotechnology/The Science and Business*. A suitable reactor could be based on batch processing, could be a continuous-flow type, could be based on plug flow, or it could be fluidized bed. Cotton fiber could be mechanically immobilized itself within the reactor, or simply packed loosely into the reactor, so that the reactants can flow through the cotton fiber. Suitable screening or filtering could be used to retain cotton fiber within the reactor, while allowing the substrates to flow into the reactor and the reactants to flow out. Cotton fiber could also be incorporated into woven substrates, filters, sheets, or other materials which could be included in such a reactor, and accomplish other processes, such as filtration of separation, at the same time as enzymatic processes are performed.

The following examples describe both the isolation of mRNA from fiber specific cells, the screening of such mRNA to isolate fiber specific clones, and the derivation of fiber specific promoters from those clones. Thereafter a method is described which has been utilized successfully to prepare transgenic cotton. A further example describes what is intended to be an exemplary illustration of a transgenic cotton plant expressing an enzyme within its fiber, which is demonstrated to be catalytically active while trapped within the cotton fiber lumen. A final example describes the stable immobilization of parathion hydrolase, an exemplary bioremedial enzyme, into cotton fibers. The ability of immobilized parathion hydrolase to actively degrade parathion is demonstrated. Further, the parathion hydrolase gene was prepared for delivery into cotton either with or without a signal peptide and in the form of a fusion protein with a carrot extensin gene. These examples are all intended to be exemplary rather than limited. It is also understood that molecular weights and numbers of nucleotides are accurate to the extent possible, given the state of the technology, but are subject to some uncertainty due to the limitations and applicable measurement technologies.

The examples below make extensive use of a gene, and its enzymatic product, both as a reporter gene and as an exemplary enzyme. The gene is referred to as the beta-glucuronidase (GUS) gene, originally isolated from *E. coli*. The GUS enzyme catalyzes the cleavage of 5-bromo-4- chloro- 3-indoyl glucuronide (X-Gluc). The indoyl derivative produced by this cleavage undergoes oxidative dimerization to form a blue dye. Cells that produce this blue dye can be easily detected. The GUS marker system for use as a reporter gene has been described in detail by Jefferson et al. in *Proc. Natl. Acad. Sci. USA*, 83:8447– 8451 (1986) and in *Plant Mol. Biol. Rep.*, 5:387–405 (1987). The GUS gene is publicly available from the American type culture collection (Accession Number 67641), and is widely used in the genetic engineering research community. Chimeric plasmids can readily be constructed by ligating a coding sequence for the GUS gene into a cassette including a suitable promoter along with a transcription terminator. Histochemical localization of beta-glucuronidase activity of plant tissues is achieved by incubating freshly cut tissue sections in a solution of X-Gluc. X-Gluc is prepared by dissolving 5 mg in 50 microliters of dimethyl formamide and diluting it to 10 ml with 50 mM sodium phosphate buffer at pH 7.0. After staining (a few hours at 37° C.) the tissue sections are rinsed off with 70% ethanol.

A quantitative assay for GUS activity depends on the cleavage of 4-methyl umbelliferyl glucuronide (MUG) by the GUS enzyme into a flurogenic product 4-methyl umbelliferone (MU). MU is fluorescent when it is hydroxyl group is ionized. The flurogenic assay is carried out as follows. Plant tissue is homogenized in an extraction buffer (50 mM $NaH_2PO_4$, pH 7.0, 10 mM EDTA 0.1% Triton X-100 X, 0.1% sodium lauryl sarcosine, 10 mM beta-mercaptoethanol). Also included on occasion is a proteinase inhibitor PMSF at a final concentration of 20 micro grams/ml and 1% insoluble PVP. The extract, after centrifugation, is added to 1 ml of MUG buffer. The MUG-buffer is made up of 1 mM MUG in the above extraction buffer. The mixture is incubated at 37° C. and at time points of 0, 20, 40, and 60 minutes, an alloquot (100 microliters) is withdrawn and added to 1 ml of stop solution (0.2M $Na_2CO_3$). The fluorescence at each time point is measured in a fluoro-calorimeter (excitation at 365 nm, emission at 455 nm). Protein concentration of the plant extract is determined by Bradford assay (Bradford, M. (1976) *Anal. Biochem.* 72, 248–254) using a test kit from Bio-Rad Laboratories. The fluorimeter is calibrated with freshly prepared MU standards. Control plant extracts are used as standards to compensate for any quenching due to plant material, while calibrating with MU standards.

EXAMPLES

1. RNA Isolation From Fiber

The first step in the isolation of fiber-specific promoters was the isolation of RNA from cotton fiber cells. RNA was isolated from specific developmental stages of cotton fiber because a selection of fiber-specific promoters capable of regulation at different developmental stages was desired. Nevertheless, if one wished to obtain fiber-specific RNAs, RNA should be isolated only from fiber cells at any stage of fiber development.

Ten-, fifteen- and twenty-three-day-old fiber cells from Coker 312 plants were collected and quick-frozen in liquid nitrogen. The 10-day fiber cells were selected to contain genes active during the primary cell wall stage of cell development. In the 15-day cells, both primary cell wall and secondary cell wall synthesis systems are active. The 23-day-old fiber cells were selected to contain genes principally active during secondary wall synthesis.

The frozen fiber cells were powdered in a mortar in liquid nitrogen and homogenized for 1.5 minutes using a polytron in a homogenization buffer at full speed. The homogenization buffer was added at a ratio of 1:2 of tissue (weight) to buffer (volume). Homogenization buffer is: 5M guanidine isothiocyanate, 0.2M Tris-acetate (pH 8.5), 0.7% Beta-mercaptoethanol, 1% polyvinyl pyrroloidone (PVP, MW 40 Kd), and 0.62% sodium lauryol sarcosine). Beta-mercaptoethanol and PVP are added just before use.

The homogenate was filtered through Mira cloth and layered over a 1.5 ml pad of 5.7M cesium chloride as described by Chirgwin, J. M. et al. *Biochemistry*, 18:5294–5299 (1979). The homogenate was then centrifuged for 18 hours at 36,000 rpm in a SW 50.1 rotor at 20° C. After centrifugation, the RNA was collected as described by Chirgwin, et al., (supra). The RNA was then further purified by phenol:chloroform extractions and precipitations in the presence of ammonium acetate, as described for DNA by Crouse, J. and Amorese D., *Focus*, 9[2]: 3–5 (1987).

Poly $(A)^+$ RNA was obtained by oligo-(dT) chromatography as described by Maniatis, et al., in *Molecular Cloning: A Laboratory Manual*, Cold Spring Harbor Laboratory, Cold Spring Harbor, N.Y., (1982).

2. Library Construction and cDNA Clone Identification

It was desirable to screen the isolated fiber RNA to determine which RNA sequences were fiber-specific. By the term "fiber-specific" it is meant to signify a sequence that is present either only in fiber cells or in a much higher abundance in fiber cells than in other plant cells. A standard technique used to identify tissue-specific sequences is to create cDNA clones from the individual RNA molecules and then to challenge the individual cDNA clones with radioactive cDNA created from RNA isolated from different tissues. cDNA clones that hybridize to fiber cDNA, but not cDNA derived from RNA from other plant tissues, contain a cDNA made from an mRNA that is fiber-specific. These mRNAs will be under the control of a fiber-specific promoter.

Complementary DNA libraries may be prepared by any standard technique. We chose to prepare separate cDNA libraries from the mRNAs from 10-day, 15-day and 23-day-old fiber cells according to the protocol developed by D'Alessio et al., *Focus*, 9[1]:1–4 (1987). The second strand synthesis was carried out as described by D'Alessio et al., supra, for homopolymer tailing. Poly-(dC) tails were added to the double-stranded cDNA, which was annealed to poly-(dG)-tailed pBR322 plasmid vector (Bethesda Research Laboratories). *E. coli* RR1 strain was transformed with the recombinant plasmids as described by Hanahan in *DNA Cloning-A Practical Approach*, Vol. 1 (1985) p. 109–135. The transformed cells were selected on antibiotic tetracycline (12 mg/liter) containing agar plates.

The specific bacteria that harbored plasmids containing fiber-specific cDNAs were identified by differential screening. The clones in the library were transferred to nitrocellulose filters and duplicate filters were made according to Hanahan and Meselson, *Gene*, 10:63–67 (1980). About 25,000 clones were screened from the 15-day and 23-day libraries using the following procedure: Radioactive probes were prepared from poly$(A)^+$ RNA of 15-day-old and 23-day-old fiber producing cells and from poly$(A)^+$ RNA of 0-day ovule, leaf, root and flower cells. The radioactive probes were prepared as described in Maniatis (supra) from $^{32}$P-dCTP and reverse transcriptase. The radioactive probes were exposed to the filters containing the clones. Prewashing, prehybridizations, hybridizations and washings of the filters were performed as described in detail in John et al., *Proc. Natl. Acad. Sci. USA*, 81:5628–5632 (1984).

The autographic signals from duplicate filters hybridized with $^{32}$P-labelled cDNAs from the different tissues were compared and the clones which hybridized to cDNAs from fiber-producing cells, but not to cDNAs from other tissues, were identified and isolated. The identified clones were then subjected to three more cycles of differential screening as described above. This repetitive screening eliminated clones which hybridized to cDNAs from non-fiber-producing cells.

Alternatively, another method used for screening the cDNA library for fiber-specific cDNA clones was by subtractive hybridization. In general, fiber cDNA was challenged with excess RNA from different tissues. Fiber cDNA that does not hybridize to the RNA preparations remained single-stranded. These non-hybridizing cDNA sequences more likely to be fiber-specific. This procedure has been described by Duguid, et al., *Proc. Natl. Acad. Sci. USA*, 85 pp. 5738–5742 (1988).

The cDNA library from the 10-day old cells was screened using a subtractive hybridization procedure. In this procedure, first the $^{32}$P-labelled cDNA from fiber was hybridized to excess biotinylated mRNA isolated from leaf tissue. The hybridized cDNA-biotinylated mRNA hybrids and the biotinylated mRNAs were separated from unhybridized cDNA by extraction with avidin in phenol:chloroform. The streptavidin was partitioned into the organic phase along with any biotinylated nucleic acid while the single-stranded cDNA remained in the aqueous phase.

Subtractive hybridization screening of 4788 clones of the 10 day fiber cell cDNA library with leaf cell cDNAs resulted in the identification of 800 clones not present in the leaf cells. These clones were then screened with cDNAs generated from ovule, flower and root mRNAs. 79 putatively fiber-specific clones were obtained from this screening.

After obtaining fiber-specific clones, the RNA populations of the different tissues was examined to determine whether the RNA encoded by the selected cDNA clone is within the population. This procedure was a double-check that the RNA is fiber-specific. The standard molecular biological method for examining a population of RNA for the presence of a particular sequence is a northern blot. For this analysis, poly(A)$^+$ RNA from different tissues was denatured in the presence of formaldehyde and size-fractionated by electrophoresis on 1.5% agar/formaldehyde gels. (John et al., supra). The RNAs were blotted onto nitrocellulose and probed with $^{32}$P-labelled inserts of each individual clone. The clones that hybridized to only RNAs from fiber-producing cells were selected. All manipulations on plasmid DNAs such as isolation, purification on cesium chloride gradients, restriction digestion, insert purifications by gel electrophoresis and electroelutions, and $^{32}$P-labelling by nick translations are standard techniques (e.g., see Maniatis et al., supra and John et al., supra).

Several cDNA clones may correspond to the same RNA sequence. The number of unique RNA messages represented among the selected cDNA clones may be determined by cross-hybridizing the cDNA clones. Clones that hybridize to each other are generated either from the same RNA sequence or from a related RNA sequence. To screen clones, cross-hybridizing by a polymerase chain reaction (PCR) procedure (Saiki et al., *Science*, 239 pp. 487–491 (1988)) was performed followed by Southern blotting and hybridization. The PCR reaction was carried out by first mixing 10 µl of bacterial culture of the cDNA clone with 90 µl of distilled water. Twenty µl of that mixture was added to a PCR reaction buffer of 50 mM KCl, 10 mM Tris-HCl pH 8.0, 2.5 mM MgCl$_2$, 0.01% gelatin, 200 µM each of dATP, dCTP, dTTP and dGTP, 12.5 picomolar each of sense and antisense primers for pBR322, and 0.5 units of Taq polymerase. The final reaction volume was 52 µl. The PCR reactions were carried out under standard conditions in a Perkin-Elmer-Cetus thermocycler.

The amplified DNA from the PCR reactions was separated by agarose gel electrophoresis and blotted onto nitrocellulose as in Southern, *J. Mol. Biol.* 98: 503–517 (1975). One or more bacterial clones from the same group were amplified by the same procedure and the products also separated on agarose gel. The amplified insert DNAs were then excised from the gel and purified by electroelution. The purified DNAs, labelled with $^{32}$P by nick translation, were hybridized with the Southern blot and the cross-hybridizing clones identified.

After northern hybridization and tests for cross-reactivity, approximately 20 putative fiber-specific clones were identified. This number represents cDNAs from all three fiber cDNA libraries.

Although all the fiber-specific cDNAs were characterized and obtained genomic clones corresponding to these cDNAs, only two cDNA clones will be further discussed. These clones were designated H6 and E6. These cDNA clones, and their corresponding genomic clones, served as examples of the isolation and use of fiber-specific promoters.

3. Preparation of Genomic DNA and Creation of Genomic Clones.

To isolate a promoter sequence, one must isolate the DNA sequence upstream from the site of RNA transcript initiation. This was accomplished by probing a library of cotton genomic clones with the fiber-specific cDNA clones. The description below describes a genomic library created from Sea Island cotton, but other cotton varieties would be suitable. Coker 312 (another cotton variety) and Kapok (a related fiber-producing plant) libraries have been probed with the clones. It is believed that fiber-specific promoters isolated from different cotton varieties are effective in other cotton varieties.

Genomic DNA from Sea Island cotton was prepared according to the methods of E. Richards described in *Current Protocols in Molecular Biology*, (Eds. Ausbel, F. M. et al.) Wiley, (1987) pp. 2.3.1–2.3.3, with the following modification: the frozen plant material was homogenized in extraction buffer containing 1% polyvinyl pyrrolidone. The purified genomic DNA was digested with restriction endonucleases and transferred to nitrocellulose filters by the Southern blotting technique. Southern, E. M., *J. Mol. Biol.*, 98:503–517 (1975).

The filters were then probed with nick-translated inserts of the fiber-specific cDNA clones. The hybridization and blot washing conditions were described in John et al. (supra). The results of such a hybridization indicated whether or not the CDNA sequences were represented in the cotton genomic DNA. Upon this hybridization, it was found that the fiber-specific cDNAs were represented in the cotton genome.

Sea Island cotton genomic libraries were prepared by ligation of the digested cotton DNA into a vector. The cotton genomic library was constructed by Clonetec, Inc., of California, in EMBL-3 vectors. Genomic inserts of about 10–15 Kb were present in the EMBL3 phage library. The phage library was plated on *E. coli* NM 538 as described in *Current Protocols in Molecular Biology*, (supra, p. 6.0.1–6.8.5).

The phage library was screened with radioactive fiber-specific cDNA inserts. A number of phage that hybridized to H6 and E6 cDNA clones were identified. Genomic clones chosen for further examination are described below. The nomenclature for the genomic clones is as follows: EMBL= Lambda vector; SI=Sea Island; E6 =cDNA insert that hybridizes to genomic clone; the last number corresponds to different genomic clones from a given library. A total of eight different genomic clones corresponding to our fiber-specific cDNA clones were obtained. From these genomic clones, regions with promoter activity were isolated. SEQ ID NO: 1 and 2 give sequence information for two of the best characterized fiber-specific promoters.

For some of these clones, cross-hybridizing genomic clones from other cotton species have been identified. For example, two different genomic clones from the Sea Island cotton library hybridize to E6 cDNA, as well as two genomic clones from the Coker 312 cotton library and one genomic clone from a Kapok library.

Set forth below more detail concerning the isolation of two of the fiber-specific promoters, the H6 gene promoter and the E6 gene promoter. One wishing to practice the present invention could isolate fiber-specific cotton promoters from a cotton genomic library by either going through a differential screening and obtaining a fiber-specific cDNA to use as a probe, as described above, or using sequences corresponding to those described here as probes to isolate corresponding promoters from the cotton genome.

H6 and E6 RNAs have been characterized to further understand the nature of the H6 and E6 promoters. It has been demonstrated that H6 RNA is tissue-specifically expressed in fiber cells, and that H6 RNA is a moderately abundant mRNA in fiber. E6 is an abundant, developmentally regulated mRNA predominantly expressed in fiber.

4. Determination of Fiber-Specific Promoters.

(a) In General

Once a genomic clone has been isolated, one must identify the DNA fragments within the large genomic insert that contained promoter activity. Comparison of the genomic clone with the corresponding cDNA clone will demonstrate which part of the genomic insert contains the upstream sequence. This comparison may be done through restriction mapping of both clones or hybridization of the cDNA clone to different restriction fragments of the genomic insert. Once a fragment with promoter activity has been identified, this fragment may be subcloned into a more convenient vector system.

(b) E6 gene promoter

The E6 genome clone, pEMBLSIE6-3, contained a 15 Kb insert. FIG. 1 is a diagram of the subcloned E6 genomic clone. A 9.5 Kb Sal I fragment of the 15 Kb insert hybridizes to E6 cDNA. This fragment was subcloned into a phagemid vector Bluescript Sk+ (Stratagene, La Jolla, Calif.). Ligated DNAs were transformed into *E. coli* strain XL-1 Blue (Stratagene). Recombinant clones selected on the basis of blue/white selection on X-gal, IPTG (5-bromo-4-chloro-3-indoyl-beta-D-galactopyranoside; isopropyl-beta-thio-galactophyranoside) plates were then analyzed by SDS-agarose gel electrophoresis (Sekar, V., *Biotechnigues*, 5:11–13, 1987). The clones were characterized by restriction mapping and Southern analysis. (*Current Protocols in Molecular Biology*, supra). If necessary, the region of the genomic insert that hybridizes to the cDNA clone was also determined. The above protocols enabled determination of the approximate boundaries of a given gene.

After ligation using T4 DNA ligase and transformation using XL-1 Blue cells, a shorter version containing the intact E6 gene was obtained. According to sequence analysis of the coding region of the genomic clone, the region between the unique Nco I and Sal I site is the 5' untranslated region and contains the promoter element for E6 gene. SEQ ID NO: 1 is the sequence of the 5' end of the E6 gene and thus contains the active E6 promoter.

(c) H6 gene promoter

Figure 2:
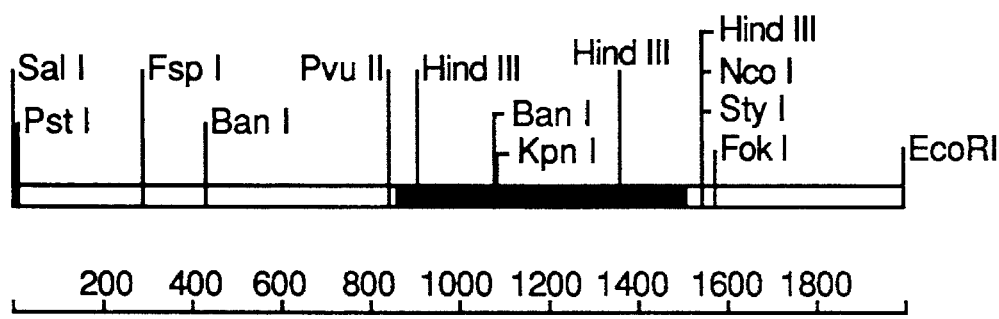
FIG. 2 is a schematic illustration of the subclone of the H6 promoter.
Figure 2:
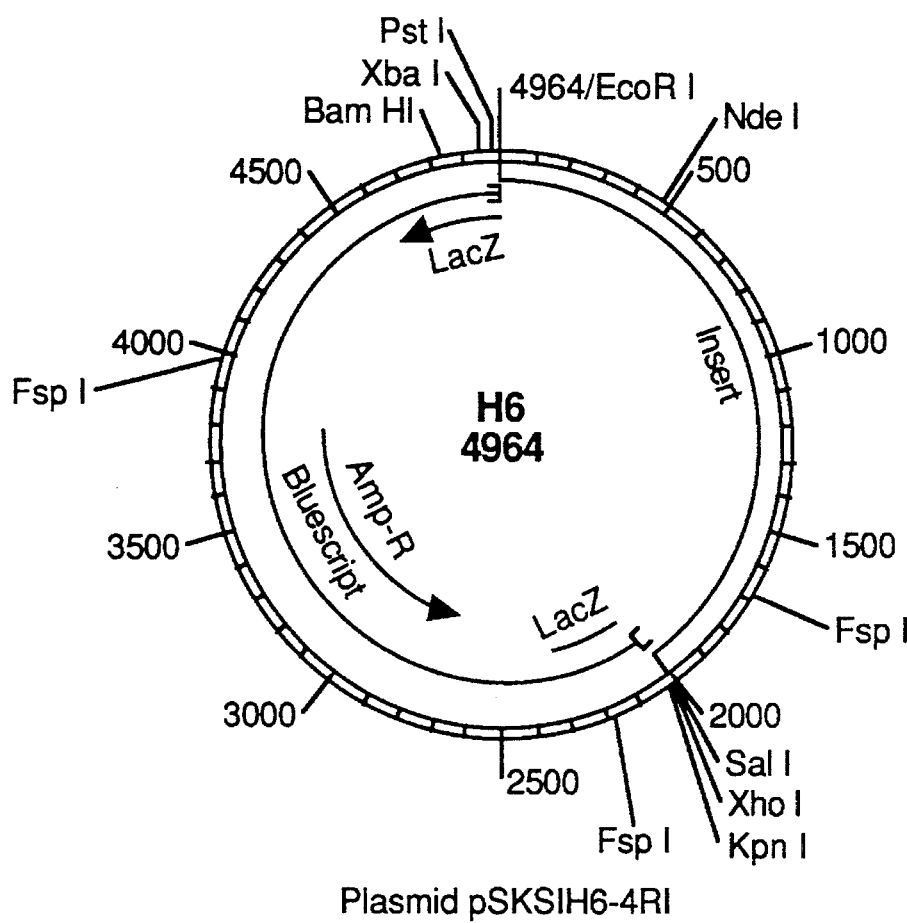

The 13 Kb Sal I fragment from the H6 genomic clone, EMBLSIH6-4, was subcloned into Bluescript SK+ vector and designated pSKSIH6-4. FIG. 2 illustrates the subcloned genomic clone. The restriction fragment of pSKSI6-4 that hybridized to the H6 cDNA was identified through filter hybridization. This fragment was religated into SK+ vector. The resulting plasmid, designated pSKSIH6-4RI, contained the H6 gene and 300 bases upstream from the initiation codon. The complete sequence of the H6 gene and the 300 bases upstream were determined. These upstream sequences are presented at SEQ ID NO: 2. Digestion with the enzyme Fsp I releases this 300 bp upstream region, together with 250 bp of vector sequence.

(d) Determination of E6 and H6 Promoter Activity

Once one has obtained a piece of DNA with a putative promoter function, it is necessary to determine whether or not the sequence is capable of controlling transcription. This may be accomplished by ligating the putative promoter into a plasmid containing a marker gene, but no promoter, and assaying for the expressing of the marker gene. Such a system was constructed, along with the appropriate controls, to assay the function of the fiber-specific promoters.

Figure 3:
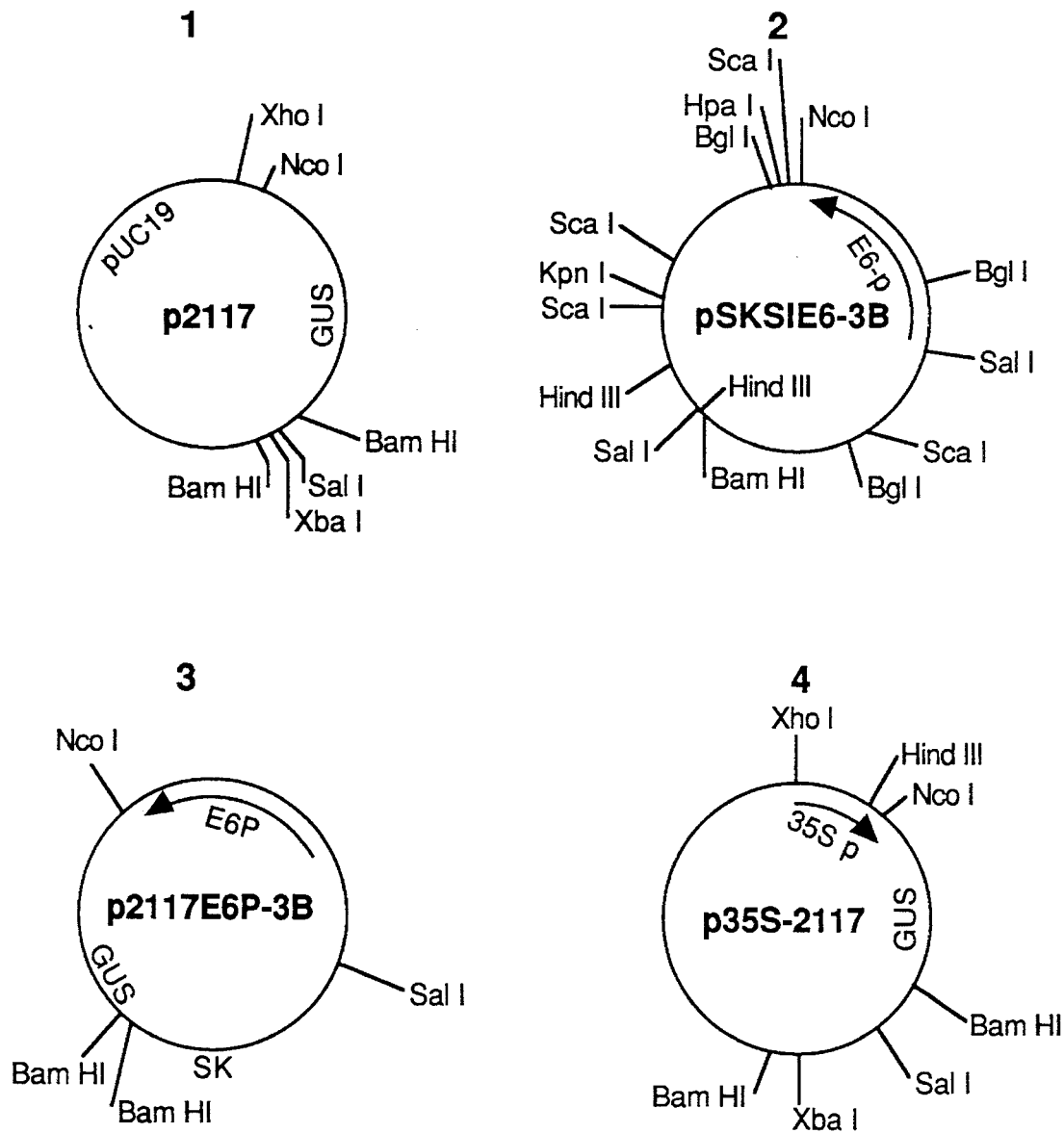
FIG. 3 illustrates schematically a set of promoter and gene sequences used in Example 4(d) below.

FIG. 3 illustrates the plasmids used in the assay system. Basically, the system used four plasmids. The first plasmid contained a marker gene, but no promoter. The second plasmid, contained only the putative promoter. The third plasmid, p 2117 E6P-3B, contained the marker gene and putative promoter. The fourth plasmid p 35s- 2117, contained a proven promoter and a marker gene. After transformation, expression by the third and fourth plasmids, and not by the first and second, indicates that the fragment has promoter ability. Obviously, such a system is not suitable for assaying whether or not the promoter is tissue-specific. In vivo plant experiments, in which the presence of the gene product in different tissues is examined, determine whether the promoter is fiber-specific.

To construct a fusion of the putative E6 promoter and a marker gene, the plasmid pSKSIE6-3B containing E6-3B gene was digested with Nco I/Xho I and a 2.5 kb 5' end of E6 gene was gel purified and subjected to Elutip-d column elution. Plasmid 2117 containing Gus gene, but no functional promoter, was digested with Nco I/Xho I and purified as above. The 2.5 kb putative promoter fragment was then ligated to 2117 at the Nco/Xho sites and transformed into XL-I cells. Recombinant clones designated p2117E6P-3B were identified by SDS-agarose gel electrophoresis. The plasmid construct now contained a putative promoter (E6). The Gus marker coding region, and a nopaline synthase polyadenylation addition signal. It could then be introduced into plant tissues through particle bombardment to test promoter function.

Plasmid p2117E6P-3B was introduced into cotton hypocotyls through particle acceleration method similar to that described in McCabe, D., et al., *Biotechnology*, 6:8, 923–926 (1988) and U.S. Pat. No. 5,015,580. Control experiments used plasmids p35s-2117, p2117 and pSKSIE6-3B (diagrammed in FIG. 3). Plasmid p35s-2117, containing a GUS construct with the CaMV 35S promoter, gave a positive GUS activity as expected. Plasmid p2117 (no plant promoter) and plasmid SKSIE6-3B (no GUS gene) gave negative GUS activity. Plasmid p2117E6P-3B, which contains the region 5' to the E6 gene and the GUS gene, showed GUS activity. This result indicates that an active promoter element is located in the 2.5 Kb NcoI/XhoI DNA fragment. The sequence 5' to the coding region starting at the initiation codon was subjected to computer analysis to locate regulatory elements, such as TATA consensus sequences. TATA box sequences were identified at positions 66, 82, 135, and 151. In addition, we have generated transgenic cotton plants containing a carrot extensin gene (SEQ. ID. NO. 5) and E6-3B promoter. Examination of RNA from leaf, root, stem, fiber and ovule of these transgenic plants, by Northern analysis, show that carrot extensin is expressed in fiber only. This result confirms that E6-3B promoter can be used to express a foreign protein preferentially in cotton fiber.

5. Plant Transformation Protocol.

The plant transformation protocols were performed using an explosive spark discharge particle acceleration apparatus. This apparatus, its theory of operation, and its utility for transferring genes into plant tissues in general are described in U.S. Pat. No. 5,015,580, which describes a plant transformation process adapted for soybean. The apparatus and its method of use are similar as used with cotton here. Therefore the specification and drawings of said U.S. Pat. No. 5,015,580 is herewith incorporated by reference, so that repetition of the description of the particle acceleration device is incorporated herein. The method of using this device, particularly insofar as it differs from the method utilized with soybean, will be described below. It is also to be understood that other particle acceleration apparatus, such as the Bio-Rad (also known as Biolistics) PDS-1000 or PDS-2000 particle acceleration instruments may also be used within the process of the present invention. It is understood that various other accelerated-particle apparatus are being developed, and many of them will also be suitable for use in this process.

The cotton transformation system utilized here began with commercial or elite cotton seed which was first surface sterilized. Cotton plants of variety DP-50 were utilized.

A sieve beaker system was autoclaved. A sieve beaker system is a beaker with dozens of holes drilled in its bottom that can be nested inside a non-drilled glass beaker. It is also useful to utilize a third sterile beaker for rinsing the seeds so that the sieve beaker can be rested in the sterile beaker while discarding wash water.

The sieve beaker was filled with cotton seeds. The beaker into which the sieve beaker is nested was then filled with to a mixture of 50% chlorox bleach so as to cover the seeds and the seeds were allowed to rest within the bleach solution for three minutes. The bleach is drained and the seeds were then rinsed five times with distilled water.

The surface sterilized cotton seeds were then placed in a sterile glass beaker. A cotton antibiotic sterilization medium was added to the beaker at twice as much volume as there are seeds. This medium consists of sterile distilled water to which has been added carbenicillin at 200 mg per liter, cefotaxime at 125 mg per liter, and 30 mg each of Bravo WP, Benlate 50 DF, and Captan 50 WP per liter. The seeds were incubated in the sterilization medium for three to four hours in the dark at room temperature.

Then the seeds were drained by pipette. The beaker was refilled with fresh cotton antibiotic sterilization medium and the seeds are incubated for an additional three hours.

The seeds were then drained and incubated overnight at 15° C. in the dark to germinate. If germination proceeds appropriately, the seed germination was suspended by refrigeration at 4° C., for up to three days following the germination process.

After the germination of the seeds, or the removal of the germinated seeds from storage, seeds were selected—that are just beginning to germinate. Overly germinated or ungerminated seeds were discarded. The proper stage of germination was defined as fully imbibed seeds with one to four millimeters of the radicle exposed. Under sterile conditions, the seed axis was removed out of the seed. This was done by manual manipulation with gloved hands to remove the seed axis from both of its cotyledons and its seed coat. The process was relatively easy to perform with practice. It is possible to readily develop the ability to pop the seed coat axis apart from the seed, without damaging the seed axis, or leaving any of the cotyledon on the seed axis.

The excised seed axis was then washed in three to four rinses of sterile distilled water. The washed but undissected explants were either dissected immediately or stored by plating on standard OR ccb medium made with fresh benzylaminopurine or BAP, but no NAA. This media is described by Barwhale et al., *Planta*, 167, pp. 473–481 (1986), but without the NAA hormone. The explants were plated on the agar surface by being laid on their side. The excised embryonic seed axis plated on the agar medium are incubated at 15° C. in the dark over night.

The washed seed axis explants were now ready for micro dissection to expose the meristems of the seed axes. This dissection was performed under sterile distilled water and with sterile tools. The dissection consists of removing the embryonic leaf, or leaves if there is more than one, that obscure the meristem on each of the excised seed axes. The fully dissected explants were transferred to another petri dish containing sterile distilled water.

After all the dissections are completed, the explants were again washed in three to five rinses of sterile distilled water. The free water was removed by pipette after the final rinse. The treated explants were then laid on their side on the surface of standard OR ccb medium made with fresh BAP but not NAA. The explants were incubated overnight, or for 24 hours maximum, at 15° C. in the dark. The treated excised embryonic axes with exposed meristems were now ready for the accelerated particle transformation blast.

To prepare the transformation particle, ten milligrams of amorphous crystalline gold powder, or of an equal mixture of 1–3 micron gold spheres and crystalline gold powder was measured into the bottom of a 1.5 milliliter Eppendorf microfuge tube. Care was taken to ensure that the gold did not spill on the sides of the tube, since that would make it difficult to resuspend the gold due to the small volumes used in the preparation process. 100 µl of 0.1M spermidine (free base) was added to this microfuge tube and the microfuge tube is vortexed well. To the microfuge tube was then added 1 to 20.0 micrograms of double-stranded DNA of the genetic construct and the tube was then vortexed gently but completely. While the DNA/carrier particle mixture was gently vortexed, 100 microliters of 2.5M $CaCl_2$ is added to the tube. Then the vortex was ceased, and precipitation was permitted for 10 minutes at room temperature. The preparation could be stored at this point for some time. Shortly before use, the mixture of DNA and carrier particles was given a brief spin in a microfuge. The cleared supernatant was removed completely, and the precipitant consisting of the DNA and carrier particles were resuspended in 20 milliliters of 100% ethanol. The resuspended DNA and carrier particle mixture was then sonicated in a water bath sonicator for two to three brief one second exposures. The resulting suspension was then coated onto the carrier sheet, at a calculated rate of 0.05 milligrams per square centimeter of the carrier sheet. After allowing the gold to settle, the excess ethanol was drained away and the sheet is dried. These preparations of DNA and carrier beads were made fresh daily.

At this point in the process, the carrier sheets are placed upon the apparatus of the type described in U.S. Pat. No. 5,015,580 for the blasting process. The cotton explants were plated on 12% xanthan gum target plates. Using the normal germination and pre-blast hormone treatments described above, typically 25 explants were found to fit on each of the target surface within the blast area.

The parameters used for the particle-mediated transformation blast itself included a relatively high electric discharge voltage through the gun, typically in the range of 15–25 kilovolts. The standard voltage used was 18 KV. The voltage is adjusted to achieve a level of impact on the treated axes such that the rate of survival of the meristems was between 40% and 90%. In other words, the blast force is adjusted to a level such that at least some of the meristems were rendered non-viable by the process. The blasting experiments were conducted in a vacuum of 350 milliliters of mercury, with helium introduced at a rate of 1.5 liters per minute at atmospheric levels, and approximately 5.0 liters per minute under the vacuum.

Each of the target tissues were blasted once or twice during the same day; target tissue blasted twice in the same day are blasted once in the .morning and once in the afternoon, with the explants stored between successive blasting procedures in a moist chamber at approximately 28° C. in the dark. The target tissues were placed in the dark immediately after each blasting exposure.

The explants were then removed from the target surface, and plated in a normal orientation on OR ccb medium made with fresh BAP but no NAA. Care was taken not to expose the explants to excessive light. Care was exercised not to allow the meristem to come in contact with any media, and no wet plates are utilized. The fresh explants were plated and then incubated at 28° C. in the dark for one or two full days.

One day after the blasting, a preliminary assessment of transient enzyme activity was conducted on the resultant tissues. The assay was conducted at this time to check for the quality of the bead preparation protocol, and also to look specifically at the number of transformation events in the meristem, a rough approximation of which can be made by checking the transient activity of the explants at this stage. Although, due to the heavy damage from the blasting process, 10 to 60% of the meristems were sufficiently damaged so as to never produce a shoot, those same damaged meristems will, upon assay, exhibit excellent transient gene activity particularly of the GUS gene using this procedure. Thus, the tissues can be assayed at this step for the percentage of GUS activity, even though shoots are not yet evident on the meristems subjected to the procedure.

Following the initial post-blast incubation on the medium described above, the cotton explants were transferred to the dextrose-based woody plant medium (WPM), minus BAP plus carbenicillin and benomyl, in plantcons again under low light. The WPM medium mixture, based on McCown & Lloyd, *Proc. International Plant Propagation Soc.*, 30:421 (1981) was prepared as follows: $NH_4NO_3$ (400 mg/l), $Ca(NO_3)_2 \cdot 4HOH$ (556 mg/l), $K_2SO_4$ (990 mg/l), $CaCl_2 \cdot 2HOH$ (96 mg/l), $KH_2PO_4$ (170 mg/l), $H_3BO_3$ (6.2 mg/l), $Na_2MoO_4 \cdot 2HOH$ (0.25 mg/l), $ZnSO_4 \cdot 7HOH$ (8.6 mg/l), $CuSO_4 \cdot 5HOH$ (0.025 mg/l), $FeSO_4 \cdot 7HOH$ (27.8 mg/l), $Na_2EDTA$ (37.3 mg/l), Thiamine·HCL (1.0 mg/l), Nicotonic acid (0.5 mg/l), Pyridoxine·HCl (0.5 mg/l), Glycine (2.0 mg/l), Myoinositol (100 mg/l), Dextrose (20 g/l), Agar (3.0 g/l), Gelrite (1.1 g/l), Calcium gluconate (1.29 g/l), Carbencillin (200 mg/l) and Benomyl (60 mg/l). The tissues were incubated at 28° C. in the dark for one to seven days.

Following the above culturing in the dark, the plantcons were then moved to full light exposure so as to induce shoot development in the tissues under cultivation.

The plantcons were thus moved to a cultivation chamber and exposed to 16 hour light periods at 28° C. A number of cultured explants then proceed to exhibit shoot elongation and development from the plated tissues. It then became necessary to evaluate the growing shoots to ascertain the level of germ line transformation events which are achieved through this process. The assay procedure was conducted at such a point that the shoots each have developed their first leaves. Then the outermost one-third to one-half of each leaf was cut off completely across the leaf through the midrib. The leaves were then assayed for GUS activity to identify GUS-positive expressing plants.

At this point, the quality of the events were characterized depending on the level of GUS activity in the leaves. Some of the leaves exhibited only uneven or irregular GUS expression indicating chimeric plants. Based on the results below and experience with other plant systems, it was observed and verified that a transformation of the vascular system, as exemplified by the leaf petiole, correlated very well with the occurrence of a germline transformation event. Some of the leaves seemed to be totally blue, indicating putatively clonal transgenic plants. If the plant was characterized as germline transformed, the plant was transferred into rooting conditions and grown out in the greenhouse. For chimeric plants, the plant was pruned to just above the transformed leaf so as to force the axillary bud to grow from the transformed area of the plant after which it is retested.

For plants that tested negative, the leaves were removed, and the plants are cultured until newly formed leaves are regenerated. Tests are again conducted. This process is repeated three times before a final negative determination for the plants was made.

The entire process as described above, from initial plating of the seeds to the recovery of an initial generation transgenic plant requires approximately three to five weeks. Based on the initial results as described above, it is expected that approximately one mericlonal transgenic plant will occur per approximately 100 to 500 meristems exposed to the blasting process. Of the mericlonal plant produced from the process, approximately 0.1–1% will be found to have transformed germ lines.

For purposes of demonstrating this example, it was also found that certain chimeric plants were quite useful. One of the species of clonal, but non-germ line, events— which were frequently observed was the type of plants which was sometimes referred to as an "epidermal transformant." Such epidermal transformants would express the inserted gene construction throughout the epidermis of the plant, even though it was not transferred in the germline to the seed of the cotton plant. However, the cotton fiber cells do arise from epidermal cells. Accordingly, any chimeric plant which expressed the inserted DNA in the epidermal cells expressed the DNA also in the fiber. Such plants model the same effect which can be achieved from germline transformant plants, and epidermal transformant plants can be recovered for experimental use at a frequency somewhat higher than clonal transformants.

6. Testing of Transqenic Fiber.

Plants were recovered from the plant transformation protocol above which were epidermal transformant events and germline transformant events. The plants were grown to maturity and the fiber was collected from the plants. Since the genes transformed into the cotton cells contain the GUS enzyme, the following procedures were taken to test the catalytic ability of the GUS enzyme in the transgenic fiber thus produced.

a. Evidence of Enzymatic Activity

Figure 4:
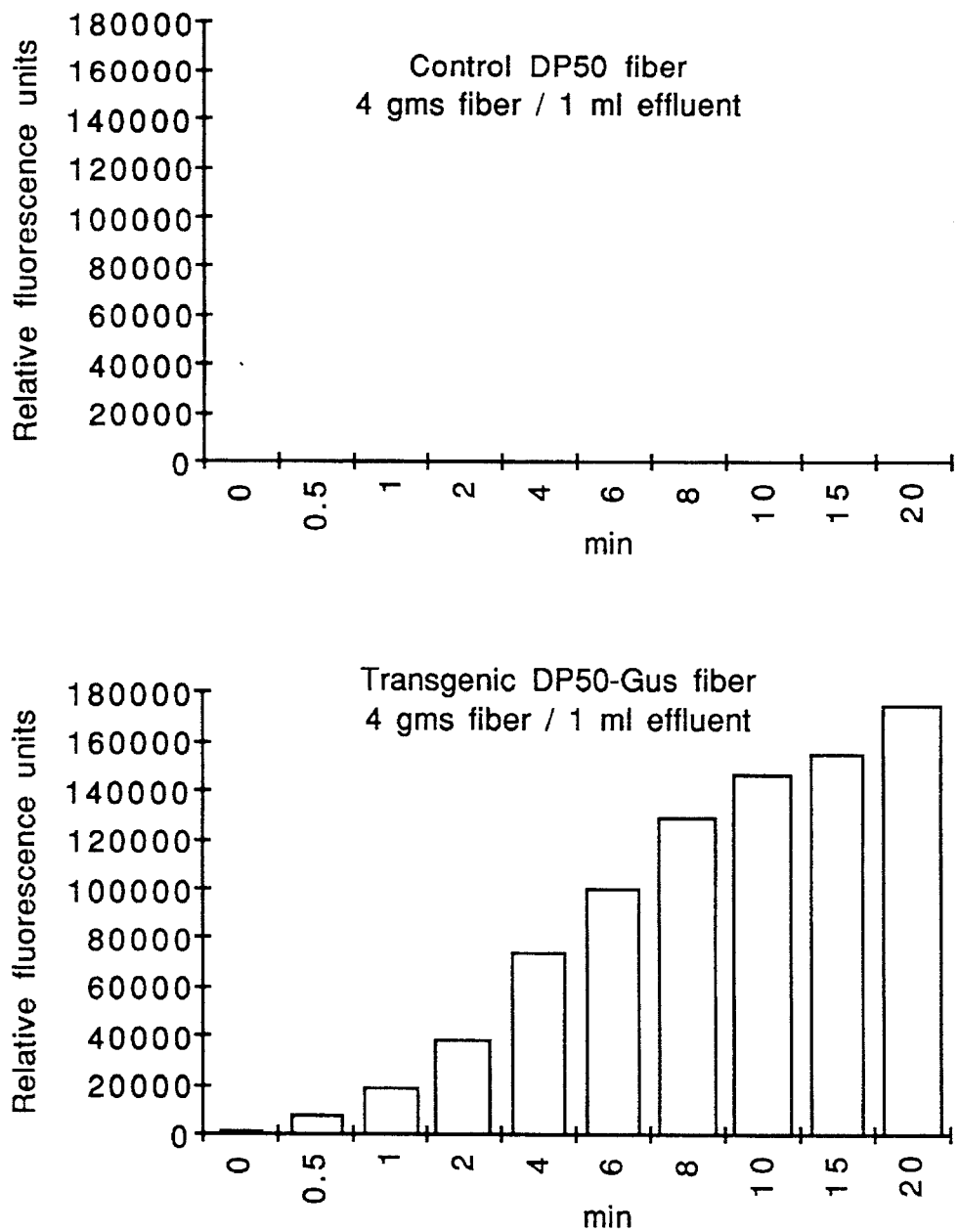
FIG. 4 is a graphical illustration of the results obtained from Example 6(a) below.

A chromatographic column was filled with 20-day old transgenic cotton fiber (approximately 4 grams, recovered from an epidermal transformant cotton plant. The column was equilibrated with modified extraction buffer (50 mM $NaH_2PO_4$, pH 7.0, 10 mM beta-mercaptothanol, and 10 mM EDTA; Triton x-100 and sodium lauryl sarcosine were omitted). After 15 minutes, the extraction buffer was removed and 10 milliliters of modified extraction buffer containing 1 milligram of MUG was added to the column. One milliliter aliquots of the extraction buffer removed from the column at intervals of ½, 1, 2, 4, 6, 8, 12, 15, and 20 minutes. The fluorescence of each of the samples were measured. The results are illustrated in FIG. 4, where they are shown in parallel along with aliquots taken from a controlled column packed with non-transgenic cotton fiber. The results clearly dramatically demonstrate that MUG, the substrate for conversion by GUS, was converted into fluorogenic product MU by the catalytic properties of the GUS enzyme present in the fiber. However, since the fiber cells were disrupted by detachment from the ovule, a possibility is that the GUS enzyme leaked out of the cells and that a portion of the substrate reaction occurred in the surrounding buffer rather than within the fiber cells themselves. However, even this experiment illustrated the utility of enzyme delivered in cotton fibers as a useful one for carrying out enzymatic reactions.

b. Activity with Intact Fibers.

The experiment described in Example 6(a) above was repeated, only this time the cotton fibers were removed as locules, that is intact fiber not detached from the ovule. Thus the biological tissue which was placed in the column consisted of a compact mass of fibers surrounding the ovules of the cotton fiber plant. Otherwise the same protocol of 6(a) above was repeated.

The reaction weight as well as the yield of the product is reduced from that measured in Example 6(a) above. The reduced rate in yield can be in part explained by the fact that the GUS enzyme is fully enclosed within the fiber and that therefore the diffusion of substrate into the fiber and the diffusion of the product out of the fiber into the buffer might be a limiting factor on the accumulation of MU in the solution. Furthermore, the number of fiber cells in direct contact with the substrate is significantly reduced when locules are used as the fiber source, due to the locules being a relatively compact and dense mass. The shielding of fibers within the locule from the substrate during the reaction period is a possible source of reduction of rate of catalysis. Despite the reduced rate of reaction, it is clear that catalysis occurs due to MUG diffusion into the cells and MU diffusion out, even though the fibers themselves are not disrupted.

c. Reutilization of the Transqenic Fiber.

Figure 5:
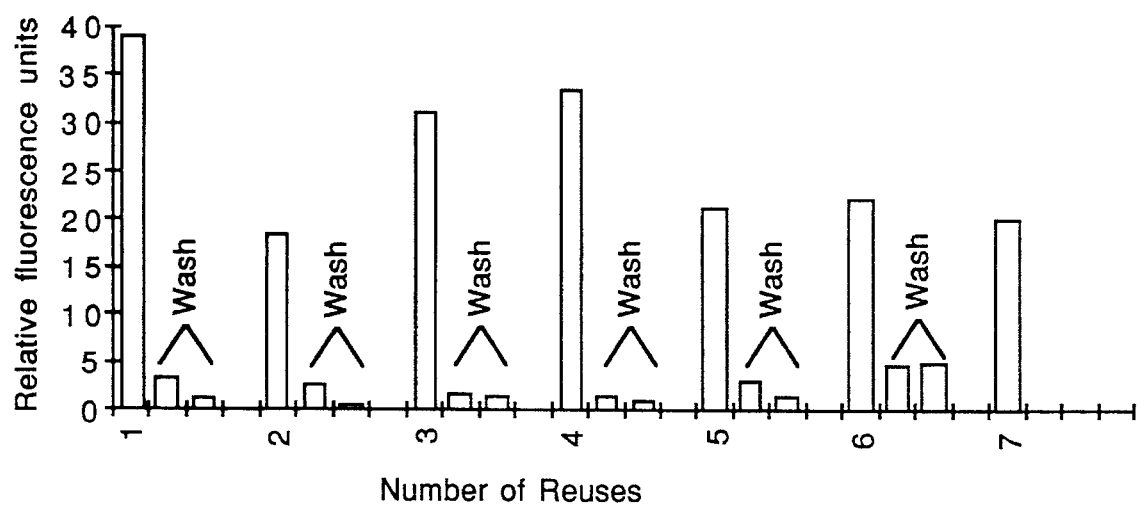
FIG. 5 is a graphical illustration of the results obtained from Example 6(c) below.

One advantage of an enzymatic system contained within cotton fiber is that the fiber can be reused a number of times thereby increasing its utility in industrial processes. To test that this could in fact occur, 38-day old transgenic intact fiber locules, approximately 2 grams thereof, was incubated at room temperature with MUG buffer for 90 minutes and the effluent was measured for fluorescence. The fiber was then washed in buffer containing no MUG until the fluorescence of the wash reached background levels. At this time, the fiber was incubated a second time with MUG for 30 minutes and the fluorescence of the resulting effluent was again measured. The washing and MUG incubation cycles were repeated seven times over a period of 72 hours. After each cycle the GUS activity was observed. These results are illustrated in FIG. 5. The experimental result thus obtained indicates that the GUS enzyme within the fiber is stable, that the enzyme is immobilized within the fiber and that the enzyme can be reused merely by recovering the cotton fiber. Thus the transgenic cotton fiber with the immobilized protein can be repeatedly used to carry out industrial processes.

d. Stability of Bound Enzyme.

In many industrial processes, the thermal stability of an enzyme is a critical parameter in obtaining efficient utilization of the enzyme system. To test the thermal stability of the cotton fiber carrying an immobilized enzyme, intact fiber locules were incubated in a buffer in the absence of MUG for 1 hour at 37° C. Following the incubation at the elevated temperature, the substrate MUG was added and the fluorescence was determined after 2 hours. Following that test, the fiber was continuously incubated at 37° C. for an additional 17 hours in buffer. At the termination of this time period, the fiber was washed, while being maintained at 37° C., in a buffer not containing MUG for 4 hours until fluorescence readings were at background levels. After the background level was reached, MUG was again added to the reaction mixture and fluorescence readings were taken after 1 hour, for a total incubation time of 22 hours.

Figure 6:
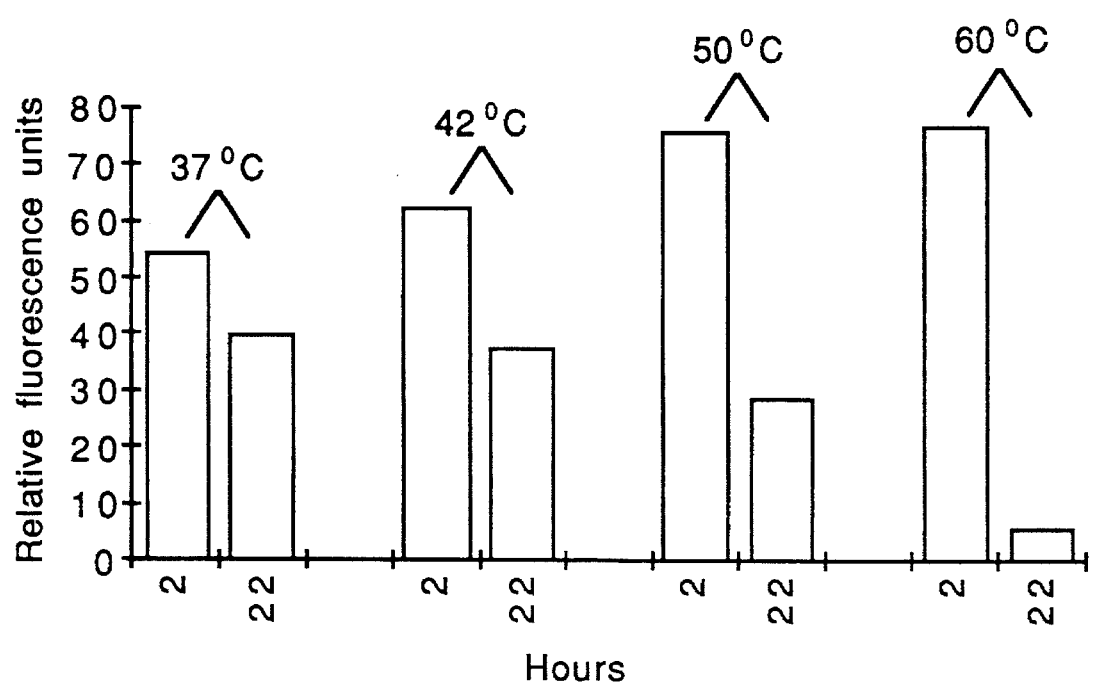
FIG. 6 is a graphical illustration of the results obtained from Example 6(d) below.
Figure 7:
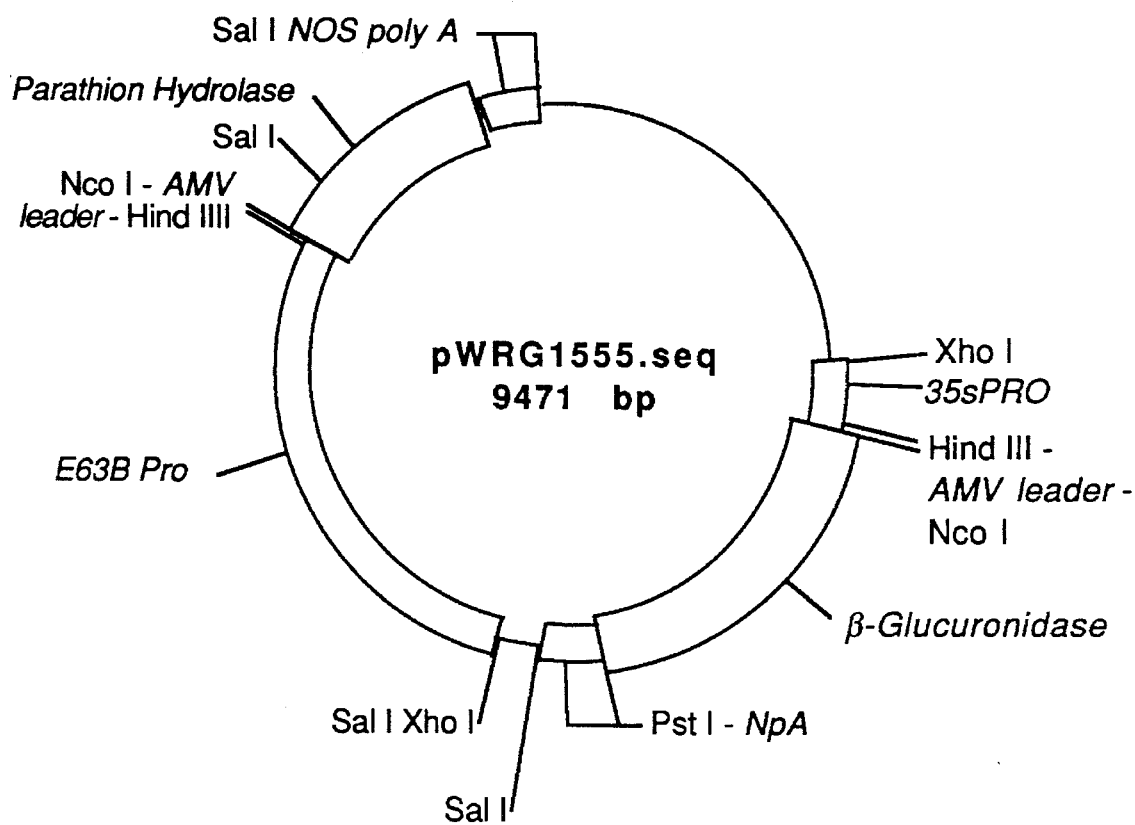
FIG. 7 is a schematic illustration of plasmid pWRG1555 that encodes an expressible parathion hydrolase gene under control of the E6-3B promoter.
Figure 8:
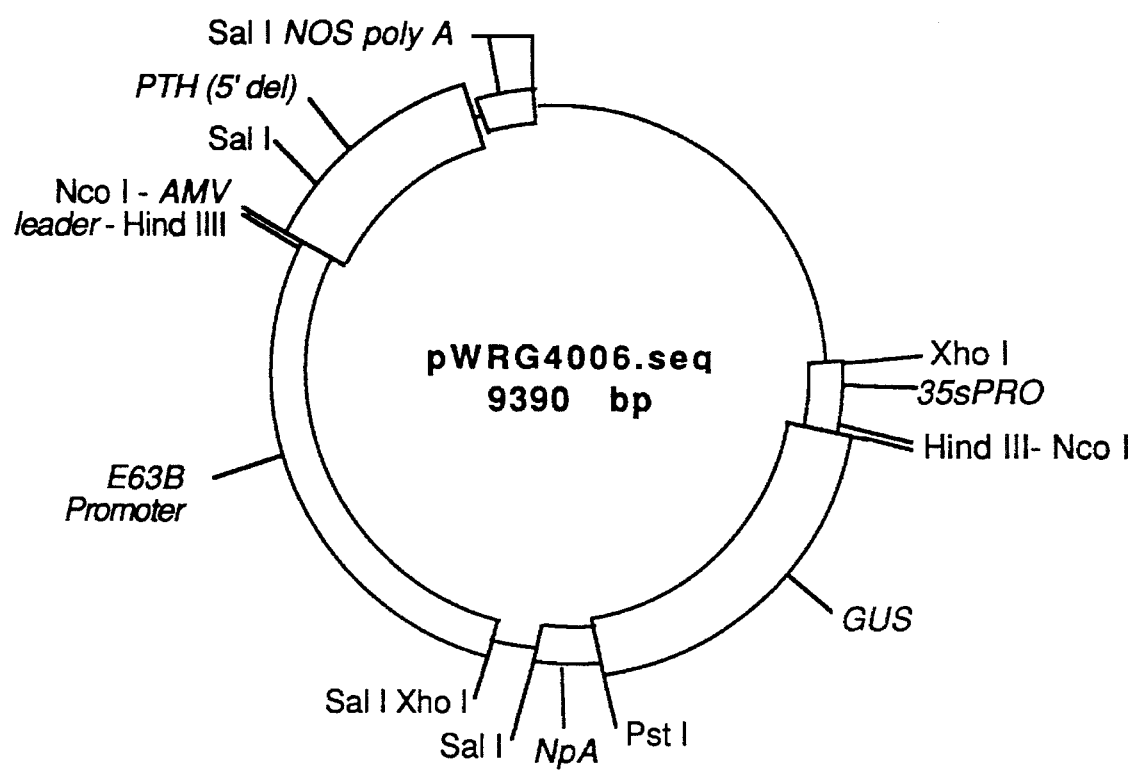
FIG. 8 is a schematic illustration of plasmid pWRG4006 that encodes an expressible parathion hydrolase gene lacking a signal peptide, under control of the E6-3B promoter.

The above process was repeated at temperatures of 42° C., 50° C., and 60° C., to determine the viability of the GUS in fiber at the elevated temperatures. The results are illustrated at FIG. 6. These results demonstrate the thermal stability of the system.

In additional experiments, intact transgenic fiber locules were maintained at 37° C., 42° C., and 50° C., for a total of 500 hours. At the termination of the incubation, the GUS activity of the fiber was tested. In each case, GUS activity was retained. When the experiment was conducted at 60° C. the GUS enzyme within the fiber was active only for 2 hours. Using a purified GUS enzyme, also incubated at 60° C., it was found that enzymatic activity could not longer be detected after 15 min. of incubation at 60° C. Similarly purified aliquots of GUS enzyme lost activity after 18 hours when incubated at 37° C., 42° C., and 50° C. Even at room temperature, the purified GUS enzyme lost 70% of its activity after 18 hours. Thus compared to free enzyme in solution, the immobilized enzyme contained within cotton fiber was stabilized and exhibited a much greater temperature stability as contrasted to the free enzyme itself.

e. Protection Aqainst Protease.

Cotton fiber being a closed tube could offer protection for enclosed enzymes/proteins against protease or other detrimental enzymes. This possibility was tested as follows. Cotton fiber locules (2 gms) were incubated in 10 mls (50 mM sodium phosphate buffer pH 7.0) containing 6 mg protease K at 37° C. for 1 hour and 12 hours. A duplicate set of locules was incubated under the same conditions, but without protease K. At the end of incubations, the locules were rinsed in buffer to remove protease and MUG containing buffer was added. Gus activity was then determined was fluorescence readings. It was found that after both 1 hour and 12 hour incubations, Gus activity was similar for both control and protease treated samples. These results indicate that fiber offers protease protection for enzymes trapped within the cell lumen.

These results demonstrate that an enzymatic protein can effectively be expressed in cotton fiber and, with or without a membrane anchoring peptide, can be stably retained within the cotton fiber as utilized in an industrial process. Furthermore, such an enzyme immobilized in a cotton fiber has increased stability. Also, surprisingly, even though the enzyme is present within the interior of the cotton fiber, substrate is capable of diffusing into the enzyme and diffusing back across the cotton fiber so that the enzyme is available for catalytic process even when physically entrapped within the cotton fiber itself. The results suggest a reusable and convenient attachment mechanism for a wide variety of proteins suitable for industrial uses, particularly ones involving catalysis.

7. Immobilization of opd gene of Flavobacterium in Cotton Fiber (a) Introduction In order to produce functional parathion hydrolase in cotton fiber, we tested three different gene constructions. Parathion hydrolase contains a hydrophobic N-terminus signal peptide that enables the protein to be targeted to the bacterial cell membrane or for excretion into the growth medium (Brown, 1980 Biochem. 12:105–112). The effect of this signal peptide on the expression level or stability in cotton fiber cells is not known. However, it is unlikely that the enzyme will be excreted when it is expressed in plant cells. Therefore we made genetic constructs with (pWRG1555) and without (pWRG4006) the signal peptide and introduced them into cotton. In addition, we also tested the effect on the enzymatic activity of parathion hydrolase when it is synthesized as a fusion protein. Extensin, a plant cell wall protein gene from the carrot, was fused to the C-terminus of the parathion hydrolase gene (pWRG4032). The constructions of these three plasmids are described below.

(b) Construction of Plasmids i. Plasmid pWRG1555—Parathion hydrolase gene with signal peptide To facilitate cloning of the parathion hydrolase gene, total Flavobacterium sp. ATCC 27551 bacterial DNA was isolated and digested to completion with Pst I. The DNA was separated by preparative gel electrophoresis and the region between 1000 and 1800 base pairs was isolated. The gene is known to be contained on a 1.3 kilobase pair Pst I fragment. The sequence of the gene was reported by Mulbry and Karns, J. Bact., 171:6740-2, 1989. The plasmid pUC18 was digested with Pst I and treated with calf intestinal phosphatase. Size selected bacterial DNA was ligated to pUC18 digested DNA and transformed into *E. coli* MM294. Colonies were selected on LB plus 100 ug/ml Ampicillin. Colonies were screened by PCR analysis using primers specific to the parathion hydrolase gene. One positive colony was selected for further restriction mapping to determine the orientation of the inserted DNA. This plasmid was called pUCPTH1. One further modification was necessary prior to insertion into a plant expression cassette. To insert an Nco I site at the 5' end of the parathion hydrolase gene, plasmid pUCPTH1 was partially digested with Eag I and the linear fragment isolated. Oligonucleotides MM148 (SEQ ID NO: 15) and MM149 (SEQ ID NO: 16) were annealled together, kinased using T4 Polynucleotide Kinase and ligated to the pUCPTH1 linear fragment. Clones were screened by restriction digestion using Nco I and Pst I (double digest). Clones giving the expected fragments (1271 bp+2700 bp) were further analyzed by DNA sequencing to confirm the insertion of the Nco I site. A correct clone was identified and called pWRG1542. This allowed the parathion hydrolase gene to be moved as an Nco I/Bam HI fragment in subsequent cloning steps.

The plant-expression plasmid pWRG1548 was made by digesting plasmid pWRG2210 with Nco I and Bam HI and isolating the 3168 bp fragment and by digesting pWRG1542 with Nco I and Bam HI and isolating the 1148 bp parathion hydrolase gene fragment. The 3168 bp fragment of pWRG2210 includes the CaMV 35S promoter and AMV leader at its Nco I end and the Nos polyA site at its Bam HI end. The two purified fragments were ligated together and transformed into *E. coli* MM294. Briefly, the pWRG1548 plasmid thus formed has the CaMV 35S promoter and the AMV coat protein 5' untranslated region upstream of the parathion hydrolase gene which is followed by the hopaline synthase (Nos) polyadenylation signal.

For fiber specific expression of parathion hydrolase in cotton, the 35S promoter of pWRG1548 was removed by digestion with Xho I and Hind III. An Xho I/Hind III fragment containing the E6-3B promoter of SEQ ID NO: 1 was inserted to generate the plasmid pWRG1550.

To provide a marker for selection in cotton transformation experiments, a Not I fragment containing a 35S promoter controlling GUS expression was inserted at the unique Not I site to generate the plasmid pWRG1555 (FIG. 7).

ii. Plasmid pWRG4006—Parathion hydrolase gene without signal peptide

To construct a plasmid lacking the putative amino-terminal signal peptide, plasmid pWRG1548 was digested to completion with Nco I and Cla I. Oligonucleotides MM175 (SEQ ID NO: 9) and MM176 (SEQ ID NO: 10) were annealed together, kinased with T4 Polynucleotide Kinase, and ligated to the 4187 bp fragment from pWRG1548. The ligation mixture was transformed into *E. coli* and colonies were screened for the 80 bp deletion between the Nco I and Cla I sites on pWRG1548. Colonies which had this deletion were sequenced to confirm the deletion and correct reading frame of the parathion hydrolase gene at the amino terminus. This plasmid was designated pWRG1592.

For fiber specific expression in cotton, the 35S promoter was switched for the E6-3B promoter as follows. Plasmid pWRG1550, described above, was digested with Hind III and Bam HI. The 3131 bp fragment containing the promoter and Nos polyadenylation fragment was isolated. Plasmid pWRG1592 was digested with Hind III and Bam HI and the 1067 bp fragment containing the AMV leader and parathion hydrolase coding region was isolated. These fragments were ligated together and transformed into *E. coli* MM294. Colonies were screened for the correct insertion by restriction mapping. The correct clone was designated pWRG4002.

To provide a screenable marker, a 2907 bp Pvu II fragment containing the 35S promoter controlling GUS expression was isolated from a plasmid. Plasmid pWRG4002 was digested to completion with Pvu II, ligated to the Pvu II GUS fragment and transformed into *E. coli* MM294 to generate plasmid pWRG4006 (FIG. 8).

iii. Plasmid pWRG4032—Parathion hydrolase/extensin fusion

To facilitate the construction of fusion peptides to parathion hydrolase, a Bgl II site was inserted near the 3' end of the parathion hydrolase coding region. Plasmid pWRG1548 was digested with Bst XI and Bam HI and the 4111 bp fragment was isolated. Oligonucleotides MM170 (SEQ ID NO: 11) and MM172 (SEQ ID NO: 12) were used to PCR amplify a 168 bp region from pWRG1548 that included the Bgl II site. The PCR generated fragment was digested with Bst XI and Bam HI, ligated to the isolated fragment from pWRG1548 and transformed into *E. coli* MM294. Colonies were screened by restriction digestion and were sequenced to confirm the Bgl II site insertion. This plasmid was designated pWRG1583.

The pWRG1583 plasmid was used to form a plasmid encoding a parathion hydroxylase/extensin fusion protein, as follows. The carrot extensin gene construction was described previously (John and Crow, 1992). The DNA sequence of the extensin gene used herein (SEQ ID NO: 5) was reported by Chen and Varner, 4 EMBO J. 2145–2151 (1985). The parathion hydrolase/extensin fusion was constructed by first digesting pWRG1583 with Bgl II and blunted-ending with DNA Polymerase and dNTPs. An Ava I/Xba I fragment containing the extensin coding region was made blunt-ended with DNA Polymerase and dNTPs. This fragment, was ligated to the pWRG1583 fragment and transformed into *E. coli* MM294. Colonies were screened by restriction digestion and a correct clone was designated pWRG1589.

Figure 9:
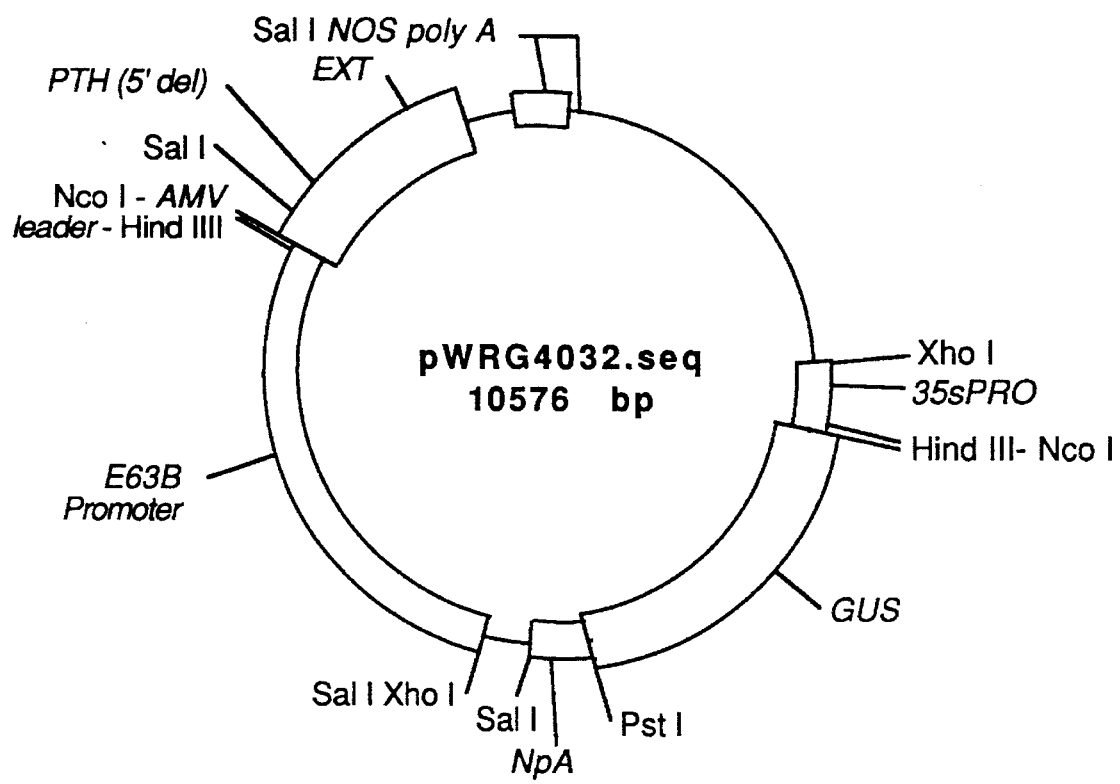
FIG. 9 is a schematic illustration of plasmid pWRG4032 that encodes a fusion protein having a parathion hydrolase gene at its amino terminus and the carrot extensin gene at its carboxy terminus. The parathion hydrolase gene is lacking its signal peptide.

To switch the E63B promoter for the 35S promoter, plasmids pWRG4002 and pWRG1589 were digested with Bam HI and Not I. The 5933 bp fragment from pWRG1589 and the 1736 bp fragment from pWRG4002 were isolated, ligated together, and transformed into *E. coli* MM294. Colonies were screened by restriction digestion and a correct clone was designated pWRG4005. Plasmid pWRG2335 was digested with Pvu II and the 2907 bp fragment containing the 35S promoter controlling GUS expression was isolated. Plasmid pWRG4005 was digested with Pvu II, ligated with the Pvu II GUS fragment from pWRG2335 and transformed into *E. coli*. Colonies were screened by restriction digestion and a correct clone was designated pWRG4032 (FIG. 9).

(c) Transformation of Cotton

Cotton transformations were carried out in cotton line DP-50 using the pWRG1555, pWRG4006 and pWRG4032 plasmid constructs as described supra in Example 5 (Plant Transformation Protocol).

(d) Testing of Transgenic Cotton Fiber

The presence of active parathion hydrolase enzyme in cotton fiber can be detected by a simple visual assay or by semiquantitative assays using parathion (0,0, Diethyl- 0-4-nitrophenyl phosphorothioate; manufactured by Riedelde Haen; Trade name, Pestanal) as a substrate. P-nitrophenol is a degradation product of parathion treated with parathion hydrolase.

i. Enzyme assays.

Fiber was collected from bolls at various days post anthesis (dpa) and frozen in liquid nitrogen. Approximately 0.5 gram of fiber was ground with a mortar and pestle to a fine powder. The ground fiber was added to 3 ml of extraction buffer (50 mM Tris-HCl pH8.5 and 0.1% (v/v) Triton X-100) and incubated at 4° C. overnight. The mixture was centrifuged at 12,000xg and the supernatant recovered. Protein concentrations were determined using a Protein Assay kit (Bio-Rad).

Parathion hydrolase activity was determined by measuring the formation of p-nitrophenol in a standard reaction mixture. The assay buffer consisted of 50 mM Tris pH8.5; 0.1% (v/v) Triton X-100; and 172 µM Parathion in a total volume of one ml. When freshly collected cotton fibers were dropped into the assay buffer (above) and incubated at room temperature for several hours, the colorless solution turned yellowish in the presence of active parathion hydrolase in fiber. Reactions were started by the addition of protein extract to reaction buffer. Samples were incubated at room temperature and the absorbance measured at 405 nm. Enzyme activity was expressed as nmol/min/ml.

ii. Transgenic Cotton Expressing Parathion Hydrolase

All together we generated 95 transgenic plants containing parathion hydrolase genes. The details of these are given in Table I. As shown in Table I, 59% to 80% of all transformants for various genes were of epidermal type. However, as the parathion hydrolase gene is expressed in the epidermal layer, epidermal transformants were sufficient to test the gene activity.

TABLE I

Transformation Frequency of Transgenic Cotton

| Plasmid | Explants Bombarded | Survived (%) | Total Transgenics (%) | Epi-dermal | Vascular |
|---|---|---|---|---|---|
| #1555 | 13,292 | 6,475 (49%) | 33 (0.51%) | 24 (73%) | 9 (27%) |
| #4006 | 10,913 | 6057 (56%) | 45 (0.74%) | 36 (80%) | 9 (20%) |
| #4032 | 12,278 | 5368 (44%) | 17 (0.32%) | 10 (59%) | 7 (41%) |

Footnote:
% Transformation is based on number of survived explants showing Gus expression
% Epidermal is based on total number of transgenics
% Vascular is based on total number of transgenics Thirty-three GUS positive transgenic cotton plants were recovered from a series of transformation experiments using the plasmid pWRG1555. Nineteen of these plants were screened for the presence of the parathion hydrolase gene by PCR analysis. When used in a PCR reaction, primers MM143 (SEQ ID NO: 13) and MM144 (SEQ ID NO: 14) amplify an 1150 bp fragment containing the parathion hydrolase gene. Seventeen of the nineteen plants screened contained an 1150 bp fragment which indicated the presence of an intact parathion hydrolase gene.

Fibers from all 33 plants were collected and assayed for parathion hydrolase activity. Initial assays involved immersing fiber in reaction buffer and observing color development due to p-nitrophenol formation. This provided a quick screen to identify plants which contained parathion hydrolase activity. These results are shown in Table II. Ten plants had detectable levels of parathion hydrolase activity. The highest expressing plant, C1409, was chosen for further analysis. In C1409, parathion hydrolase enzyme activity rises sharply between 0 and 10 dpa to about 160 nmol/min/ml then falls gradually to a baseline level at about 25 dpa. Maximal enzyme activity is observed during 10–13 dpa. Enzyme activity was shown to be stable over several weeks in 15 dpa fiber when stored at room temperature and used in repeat assays.

TABLE II

PTH Expression in Cotton Fiber Containing Plasmid #1555

| Plant # | Cultivar | Transformation | PTH activity | Gus activity |
|---|---|---|---|---|
| 1369 | DP50 | Epidermal | (+) | (+) |
| 1374 | DP50 | Epidermal | (−) | (+) |
| 1375 | DP50 | Epidermal | (−) | (+) |
| 1388 | DP50 | Vascular | (−) | (+) |
| 1390 | DP50 | Epidermal | (−) | (+) |
| 1393 | DP50 | Vascular | (−) | (+) |
| 1397 | DP50 | Epidermal | (+) | (+) |
| 1402 | DP50 | Vascular | (−) | (+) |
| 1403 | DP50 | Epidermal | (−) | (+) |
| 1404 | DP50 | Vascular | (−) | (+) |
| 1408 | DP50 | Epidermal | (+) | (+) |
| 1409 | DP50 | Epidermal | (+) | (+) |
| 1410 | DP50 | Epidermal | (+) | (+) |
| 1411 | DP50 | Epidermal | (−) | (+) |
| 1412 | DP50 | Vascular | (−) | (+) |
| 1413 | DP50 | Epidermal | (−) | (+) |
| 1414 | DP50 | Epidermal | (−) | (+) |
| 1415 | DP50 | Epidermal | (−) | (+) |
| 1823 | DP50 | Epidermal | (+) | (+) |

TABLE II-continued

PTH Expression in Cotton Fiber Containing Plasmid #1555

| Plant # | Cultivar | Transformation | PTH activity | Gus activity |
|---|---|---|---|---|
| 1834 | DP50 | Epidermal | (+) | (+) |
| 1877 | DP50 | Epidermal | (−) | (+) |
| 1906 | DP50 | Epidermal | (−) | (+) |
| 1911 | DP50 | Epidermal | (−) | (+) |
| 1913 | DP50 | Epidermal | (+) | (+) |
| 1924 | DP50 | Vascular | (−) | (+) |
| 1932 | DP50 | Epidermal | (−) | (+) |
| 1918 | DP50 | Vascular | (−) | (+) |
| 1981 | DP50 | Epidermal | (−) | (+) |
| 1984 | DP50 | Epidermal | (+) | (+) |
| 1985 | DP50 | Vascular | (−) | (+) |
| 1987 | DP50 | Epidermal | (−) | (+) |
| 4898 | DP50 | Epidermal | (+) | (+) |
| 4700 | DP50 | Vascular | (−) | (+) |

Note: 33 plants tested, 10 are positive for PTH

Northern blot analysis was done to determine the level of parathion hydrolase transcript in transgenic fiber. The expected size for this transcript is approximately 1400 nucleotides including the polyA tail. Total RNA was isolated from bolls at 15 dpa. Three plants (C1408, C1409, and C1410) showed detectable levels of parathion hydrolase mRNA at the expected size. Plant C1397 has a very low level of parathion hydrolase mRNA. Plant number C1409 was the highest expressor at 0.5 pg parathion hydrolase mRNA per 10 μg of total RNA. The peak of parathion hydrolase mRNA occurred at 10 dpa and coincided with the peak of enzyme activity. The level of parathion hydrolase mRNA declined after 10 dpa and is not detected at 25 dpa. This parallels the enzyme activity data of the previous paragraph. Total RNA was isolated and northern blot analysis done on various tissue types from plant C1409. A strong signal was detected in 15 dpa fiber, a weak signal detected in leaf tissue and no signal was detected in roots or flowers.

Tables III and IV show the results of screening of transgenic fibers from plants containing plasmid pWRG4006 and pWRG4032, respectively. A total of 23 plants were positive for parathion hydrolase expression using the quick screen from transgenic plants containing the three gene constructs (Tables II, III, and IV). However, it is likely that the quick screen may not identify plants that express only small amounts of enzyme and, therefore, we may have identified only high expressers. A time course of enzymatic activity during fiber development from plant #5599 containing the parathion hydrolase-extensin fusion protein reveals an increase in parathion hydrolase activity from baseline to about 10 nmol/min/ml at 10 dpa, a maximum activity of about 35 nmol/min/ml at 15 dpa, a decline to about 15 nmol/min/ml at 20 dpa and a return to baseline value by 30 dpa. Thus, the fusion protein retains its enzymatic activity over time. In general, we have observed that plants containing the parathion hydrolase gene without a signal peptide (pWRG4006) have the most enzymatic activity, compared to plants containing the fusion protein (pWRG4032) or the gene with signal peptide (pWRG1555).

TABLE III

PTH Expression in Cotton Fiber Containing Plasmid #4006

| Plant # | Cultivar | Transformation | PTH activity | Gus activity |
|---|---|---|---|---|
| 4548 | DP50 | Epidermal | (+) | (+) |

TABLE III-continued

PTH Expression in Cotton Fiber Containing Plasmid #4006

| Plant # | Cultivar | Transformation | PTH activity | Gus activity |
|---|---|---|---|---|
| 4576 | DP50 | Vascular | (−) | (+) |
| 4582 | DP50 | Epidermal | (−) | (+) |
| 4596 | DP50 | Epidermal | (+) | (+) |
| 4598 | DP50 | Epidermal | (−) | (+) |
| 4599 | DP50 | Vascular | (−) | (+) |
| 4601 | DP50 | Epidermal | (−) | (+) |
| 4610 | DP50 | Epidermal | (+) | (+) |
| 4618 | DP50 | Epidermal | (+) | (+) |
| 4622 | DP50 | Epidermal | (−) | (+) |
| 4627 | DP50 | Epidermal | (−) | (+) |
| 4668 | DP50 | Epidermal | (−) | (+) |
| 4844 | DP50 | Vascular | (−) | (+) |
| 4846 | DP50 | Vascular | (−) | (+) |
| 4852 | DP50 | Epidermal | (−) | (+) |
| 4866 | DP50 | Vascular | (−) | (+) |
| 4869 | DP50 | Epidermal | (+) | (+) |
| 4877 | DP50 | Epidermal | (−) | (+) |
| 4883 | DP50 | Vascular | (−) | (+) |
| 4887 | DP50 | Epidermal | (−) | (+) |
| 4890 | DP50 | Epidermal | (−) | (+) |
| 4895 | DP50 | Epidermal | (−) | (+) |
| 4900 | DP50 | Epidermal | (−) | (+) |
| 4905 | DP50 | Epidermal | (−) | (+) |
| 4905 | DP50 | Vascular | (−) | (+) |
| 4914 | DP50 | Epidermal | (−) | (+) |
| 4919 | DP50 | Vascular | (+) | (+) |
| 4921 | DP50 | Epidermal | (−) | (+) |
| 4929 | DP50 | Epidermal | (−) | (+) |
| 4998 | DP50 | Epidermal | (−) | (+) |
| 5197 | DP50 | Vascular | (−) | (+) |

Note: 31 plants tested, 6 are positive for PTH

TABLE IV

PTH Expression in Cotton Fiber Containing Plasmid #4032

| Plant # | Cultivar | Transformation | PTH activity | Gus activity |
|---|---|---|---|---|
| 5552 | DP50 | Vascular | (−) | (+) |
| 5562 | DP50 | Epidermal | (−) | (+) |
| 5568 | DP50 | Epidermal | (+) | (+) |
| 5569 | DP50 | Epidermal | (−) | (+) |
| 5570 | DP50 | Epidermal | (−) | |
| 5579 | DP50 | Vascular | (−) | (+) |
| 5599 | DP50 | Epidermal | (+) | (+) |
| 5650 | DP50 | Vascular | (++) | (+) |
| 5651 | DP50 | Epidermal | (+) | (+) |
| 5653 | DP50 | Epidermal | | |
| 5655 | DP50 | Vascular | (+) | (+) |
| 5662 | DP50 | Epidermal | | |
| 5663 | DP50 | Vascular | (+) | (+) |
| 5684 | DP50 | Vascular | (−) | (+) |
| 5835 | DP50 | Vascular | (−) | (+) |
| 5888 | DP50 | Epidermal | (+) | (+) |
| 5858 | DP50 | Epidermal | | |

Note: 17 plants tested, 7 are positive for PTH

The data presented here show that all three genetic constructs are active in cotton plants and produce a functional, stable parathion-degrading enzyme in fiber. These data demonstrate the potential for using fiber containing specific enzymes for bioremediation.

Stability of GUS and PTH Enzymes in Cotton Fiber.

Date from second 6d and e indicated that cotton fiber may provide stability to enzymes from thermal denaturation and protease attach. In order to test the effect of prolonged storage on enzymatic activities we harvested mature dry transgenic fibers from three plants and stored them at 23°–25° C. in paper bags for varying periods of time. Fibers were then tested for GUS as well as PTH activities. These results are shown in Table V. Of the three samples tested, all three tested positive for GUS while one sample (#1409) showed positive PTH reaction. This results corroborate our earlier assumption that enzymes can be produced in fiber and the fiber can be stored over long periods of time with minimal precautions for future use.

TABLE V

GUS and PTH Activities in Stored Transgenic Fibers

| Plant # | Plasmid | Date of Harvest | Date of Test | Days in Storage | GUS | PTH |
|---------|---------|-----------------|--------------|-----------------|-----|-----|
| 1397 | 1555 | 1-21-93 | 3-14-94 | 417 | + | |
| 1409 | 1555 | 1-21-93 | 3-11-94 | 413 | + | + |
| 1410 | 1555 | 1-21-93 | 3-11-94 | 413 | + | − |

We claim:

1. A method for creating an immobilized enzyme on a support comprising the steps of creating a genetic construction for the expression of the enzyme in a cotton plant, the genetic construction including a coding region for the enzyme and a promoter effective to express the coding region in the seed floss fiber cells of the cotton plant, the enzyme being operable to catalyze a reaction on substrates under the conditions prevalent in a seed floss fiber cell;

genetically transforming the genetic construction into the inheritable genetic material of the cotton plant;

cultivating the cotton plant;

harvesting the seed floss fiber produced by the cotton plant with the enzyme immobilized therein, the fiber serving as a support for the enzyme; and performing a reaction with the enzyme in its active form in the harvested fiber by exposing the harvested fiber to substrates which can be catalyzed by the enzyme.

2. A method as claimed in claim 1 wherein the promoter is selected from the group consisting of SEQ ID NO: 1 and SEQ ID NO: 2.

3. A method as claimed in claim 1 wherein the steps of genetically transforming the cotton plant includes the steps of coating copies of the genetic construction onto small biologically inert carrier particles, physically accelerating the carrier particles into meristematic tissues of the cotton plant, and culturing the meristematic tissues into a whole plant, and testing for the presence of the foreign genetic construction in the whole plant or its progeny.

4. A method of obtaining enzyme immobilized in a support comprising the steps of cultivating a transgenic cotton plant comprising in its inheritable genetic material a foreign genetic construction causing expression of the enzyme in the seed floss fiber cells of the cotton plant, the enzyme being operable to catalyze a reaction on substrates at a pH and under conditions found in a seed floss fiber cell;

recovering the seed floss fiber from the cotton plant; and using the recovered cotton fiber with the enzyme therein to catalyze the reaction catalyzed by the enzyme by exposing the recovered cotton fiber to the substrates for the reaction catalyzed by the enzyme.

5. A method of obtaining enzyme immobilized in a support comprising the steps of cultivating a transgenic cotton plant comprising in its inheritable genetic material a foreign genetic construction causing expression of the enzyme in the lumen of the seed floss fiber cells of the cotton plant, the enzyme being operable to catalyze a reaction on substrates at a pH and under conditions found in the lumen of a cotton seed floss fiber cell;

recovering the seed floss fiber from the cotton plant; and using the recovered cotton fiber with the enzyme therein to catalyze the reaction catalyzed by the enzyme by exposing the recovered cotton fiber to an aqueous solution containing the substrates for the reaction catalyzed by the enzyme.

* * * * *

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 614 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Gossypium barbadense
        ( B ) STRAIN: Sea Island
        ( F ) TISSUE TYPE: Fiber cells ( v i i ) IMMEDIATE SOURCE:
        ( A ) LIBRARY: EMBL-SI
        ( B ) CLONE: pSKSIE6-3B ( i x ) FEATURE:
        ( A ) NAME/KEY: promoter
        ( B ) LOCATION: 1..614

( x i ) SEQUENCE DESCRIPTION: SEQ ID NO:1:

```
AAATTATAGC  ATACCTCACG  ATGTGGGTGA  AGTAAAATTA  TTTAACAAAT  ATATTTTGAA   60
AAATTGATAA  AAATACTAAA  TGAGGTTTTG  GTTGAATAGT  AAGATATAAT  TATTACAAAT  120
TATAAATATG  TAGGTTCAAA  ATCTATCATG  TGTATATTTG  TACTATTATT  CTATATAAAT  180
TGATAACCTT  ATAAAAGTAT  CTAATTTAGT  TTATGGTTGA  TTGATCGATA  ATACCAAATT  240
TATTAAAAAT  TAATATTAGT  AAAGATATAT  AGTACAAAAC  TAAACATAAA  ATTTTATATG  300
TTAAGGAAAT  AGCGGAAAAA  ATATCATATT  TGTAGAACTG  TTTAGCAGTG  TGGGAGAATG  360
GGATCATTAC  AAGGAAAAAT  GAAATATATA  TCATTAATAC  CAAACATAAA  AGAAAGCGTC  420
TTTTGATAAA  GTTGTTATTG  GTGTAATGTG  AAGGGACCAC  AATCATCACC  ATTCACCACT  480
TGCTCCTAAT  TGAGTTGAAA  TCTTTTTACA  ACATAGAAAA  CTAGAAGATC  GCCCTTTCTT  540
GCTTCATATA  TATAGATTTT  GTATCATCGC  AATTTCACAT  CACACACACA  AGTAAAGCAT  600
TAGCAACCAT  AGCC                                                        614
```

( 2 ) INFORMATION FOR SEQ ID NO:2:

(i) SEQUENCE CHARACTERISTICS:
        (A) LENGTH: 320 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Gossypium barbadense
        (B) STRAIN: Sea Island
        (F) TISSUE TYPE: Fiber cell (vii) IMMEDIATE SOURCE:
        (B) CLONE: pSKSIH6-4RI (ix) FEATURE:
        (A) NAME/KEY: promoter
        (B) LOCATION: 1..320

(xi) SEQUENCE DESCRIPTION: SEQ ID NO:2:

```
GTCGACCTGC AGGTCAACGG ATCTTTTTTA GCTGTGTTTA TTAAAAAAAA TAAAAAATA      60
TAAAAGTAGT TTTTTTAGAG TAAATGTAAA ACTTTAAAAT AATTGTAATA TGTAAAATTA    120
AAAATATTAA ACTATTACA  ACCGTCGGAT TAAAAATGAT ATATTTTGA  ATGATGATGA   180
AGATCGATTC CTGATGTATA TAAATACTGC CTTCTATTCC CTTCAGTCTT CGCTTCACCC    240
ACTTTCTCAT TTCACACGGG TTGTGGCGTA GTTAAGCAG  AGAGGGTGCG CAGGATAAAG   300
CTATTCACCA TTGTTTCAAC                                                320
```

(2) INFORMATION FOR SEQ ID NO:3:

(i) SEQUENCE CHARACTERISTICS:
                (A) LENGTH: 913 base pairs
                (B) TYPE: nucleic acid
                (C) STRANDEDNESS: double
                (D) TOPOLOGY: linear (ii) MOLECULE TYPE: DNA (genomic)

(iii) HYPOTHETICAL: NO (iv) ANTI-SENSE: NO (vi) ORIGINAL SOURCE:
                (A) ORGANISM: Gossypium hirsutum
                (B) STRAIN: Coker 312
                (F) TISSUE TYPE: Fiber cells (vii) IMMEDIATE SOURCE:
                (B) CLONE: H6

(ix) FEATURE:
                (A) NAME/KEY: CDS
                (B) LOCATION: 72..716

(ix) FEATURE:
                (A) NAME/KEY: sig_peptide
                (B) LOCATION: 72..147

(xi) SEQUENCE DESCRIPTION: SEQ ID NO:3:

```
TTTCACACGG GTTGTGGCGT AGTTTAAGCA GAGAGGGTGC GCAGGATAAA GCTATTCACC     60

ATTGTTTCAA C ATG AAG GTT TGT AAT AAA AAT TTG TTT CTA TCA GCA TTG    110
             Met Lys Val Cys Asn Lys Asn Leu Phe Leu Ser Ala Leu
               1               5                  10

CTT TGC ATT GCT GTT GCA GGA GTT TTG GGT CAA GCT CCT AGT AAT CCT     158
Leu Cys Ile Ala Val Ala Gly Val Leu Gly Gln Ala Pro Ser Asn Pro
```

|  |  |  |  |  | 15 |  |  |  |  | 20 |  |  |  |  | 25 |  |  |
|---|---|---|---|---|---|---|---|---|---|---|---|---|---|---|---|---|---|
| CCT | ACG | TCT | ACG | CCG | GCG | ACA | CCC | ACA | CCA | CCG | GCT | TCT | ACT | CCT | CCT | | 206 |
| Pro | Thr | Ser | Thr | Pro | Ala | Thr | Pro | Thr | Pro | Pro | Ala | Ser | Thr | Pro | Pro | | |
| 30 | | | | | 35 | | | | | 40 | | | | | 45 | | |
| CCG | ACG | ACT | CAA | GCA | CCG | CCT | ACA | CCA | ACC | GCC | ACT | CCG | CCA | CCG | GTT | | 254 |
| Pro | Thr | Thr | Gln | Ala | Pro | Pro | Thr | Pro | Thr | Ala | Thr | Pro | Pro | Pro | Val | | |
| | | | 50 | | | | | 55 | | | | | 60 | | | | |
| TCT | ACT | CCT | CCT | CCC | ACT | TCA | TCA | CCG | CCC | CCA | GTG | ACA | GCT | TCT | CCA | | 302 |
| Ser | Thr | Pro | Pro | Pro | Thr | Ser | Ser | Pro | Pro | Pro | Val | Thr | Ala | Ser | Pro | | |
| | | | 65 | | | | | 70 | | | | | 75 | | | | |
| CCC | CCA | GTT | TCA | ACT | CCT | CCA | CCC | AGT | TCT | CCT | CCT | CCT | GCA | ACT | CCA | | 350 |
| Pro | Pro | Val | Ser | Thr | Pro | Pro | Pro | Ser | Ser | Pro | Pro | Pro | Ala | Thr | Pro | | |
| | | 80 | | | | | 85 | | | | | 90 | | | | | |
| CCA | CCT | GCT | TCT | CCT | CCT | CCT | GCA | ACT | CCA | CCT | CCA | GCT | TCT | CCA | CCT | | 398 |
| Pro | Pro | Ala | Ser | Pro | Pro | Pro | Ala | Thr | Pro | Pro | Pro | Ala | Ser | Pro | Pro | | |
| | 95 | | | | | 100 | | | | | 105 | | | | | | |
| CCT | GCC | ACT | CCT | CCA | CCA | GCT | TCT | CCA | CCT | CCC | GCC | ACT | CCA | CCA | CCT | | 446 |
| Pro | Ala | Thr | Pro | Pro | Pro | Ala | Ser | Pro | Pro | Pro | Ala | Thr | Pro | Pro | Pro | | |
| 110 | | | | | 115 | | | | | 120 | | | | | 125 | | |
| GCA | ACC | CCA | CCG | CCA | GCA | ACT | CCT | CCT | CCT | GCT | ACC | CCA | CCA | CCA | GCT | | 494 |
| Ala | Thr | Pro | Pro | Pro | Ala | Thr | Pro | Pro | Pro | Ala | Thr | Pro | Pro | Pro | Ala | | |
| | | | 130 | | | | | 135 | | | | | 140 | | | | |
| CCA | TTG | GCT | TCT | CCT | CCA | GCC | ACA | GTC | CCA | GCT | ATC | TCT | CCA | GTA | CAA | | 542 |
| Pro | Leu | Ala | Ser | Pro | Pro | Ala | Thr | Val | Pro | Ala | Ile | Ser | Pro | Val | Gln | | |
| | | | 145 | | | | | 150 | | | | | 155 | | | | |
| ACA | CCA | TTG | ACC | TCG | CCA | CCA | GCT | CCG | CCG | ACC | GAG | GCC | CCA | GCA | CCT | | 590 |
| Thr | Pro | Leu | Thr | Ser | Pro | Pro | Ala | Pro | Pro | Thr | Glu | Ala | Pro | Ala | Pro | | |
| | | 160 | | | | | 165 | | | | | 170 | | | | | |
| ACC | CTC | GGG | GCT | GCT | ACG | CCA | GGT | CCA | GCT | GGA | ACA | GAC | ACG | AGC | GGA | | 638 |
| Thr | Leu | Gly | Ala | Ala | Thr | Pro | Gly | Pro | Ala | Gly | Thr | Asp | Thr | Ser | Gly | | |
| | | 175 | | | | | 180 | | | | | 185 | | | | | |
| GCA | AAT | CAA | ATG | TGG | ACC | GTA | CAA | AAG | ATG | ATG | GGA | AGC | TTA | GCC | ATG | | 686 |
| Ala | Asn | Gln | Met | Trp | Thr | Val | Gln | Lys | Met | Met | Gly | Ser | Leu | Ala | Met | | |
| 190 | | | | | 195 | | | | | 200 | | | | | 205 | | |
| GGA | TGG | GCT | CTG | CTC | AAT | CTG | ATG | GTT | TAAAACAACC | GTGTGCCTCA | | | | | | | 733 |
| Gly | Trp | Ala | Leu | Leu | Asn | Leu | Met | Val | | 215 | | | | | | | |
| | | | 210 | | | | | | | | | | | | | | |

| CATTTGATGC | CATAGCTGTG | TAATGTTTCA | TTCAATTGCT | TATTTCGGCC | TTGTTTTTCT | 793 |
| CGTATTTTAT | GGGCTGATGT | CTCATATGGG | ACTTTTCTAC | TATACGTATA | TGAGAGCCTA | 853 |
| CATTACTTTA | CCATTATATT | GTATTCTTTG | AGACATTATT | ATTATTTTTT | TACCTTTTGA | 913 |

( 2 ) INFORMATION FOR SEQ ID NO:4:

( i ) SEQUENCE CHARACTERISTICS:
        ( A ) LENGTH: 214 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Met | Lys | Val | Cys | Asn | Lys | Asn | Leu | Phe | Leu | Ser | Ala | Leu | Leu | Cys | Ile |
|---|---|---|---|---|---|---|---|---|---|---|---|---|---|---|---|
| 1 | | | | 5 | | | | | 10 | | | | | 15 | |

| Ala | Val | Ala | Gly | Val | Leu | Gly | Gln | Ala | Pro | Ser | Asn | Pro | Pro | Thr | Ser |
|---|---|---|---|---|---|---|---|---|---|---|---|---|---|---|---|
| | | | 20 | | | | | 25 | | | | | 30 | | |

| Thr | Pro | Ala | Thr | Pro | Thr | Pro | Ala | Ser | Thr | Pro | Pro | Thr | Thr |
|---|---|---|---|---|---|---|---|---|---|---|---|---|---|
| | | | 35 | | | | | 40 | | | | | 45 |

| Gln | Ala | Pro | Pro | Thr | Pro | Thr | Ala | Thr | Pro | Pro | Val | Ser | Thr | Pro |
|---|---|---|---|---|---|---|---|---|---|---|---|---|---|---|
| | 50 | | | | | 55 | | | | | 60 | | | |

```
Pro  Pro  Thr  Ser  Ser  Pro  Pro  Val  Thr  Ala  Ser  Pro  Pro  Pro  Val
65                  70                  75                            80

Ser  Thr  Pro  Pro  Pro  Ser  Ser  Pro  Pro  Pro  Ala  Thr  Pro  Pro  Pro  Ala
               85                       90                       95

Ser  Pro  Pro  Pro  Ala  Thr  Pro  Pro  Pro  Ala  Ser  Pro  Pro  Pro  Ala  Thr
               100                      105                      110

Pro  Pro  Pro  Ala  Ser  Pro  Pro  Pro  Ala  Thr  Pro  Pro  Pro  Ala  Thr  Pro
          115                      120                      125

Pro  Pro  Ala  Thr  Pro  Pro  Pro  Ala  Thr  Pro  Pro  Pro  Ala  Pro  Leu  Ala
     130                      135                      140

Ser  Pro  Pro  Ala  Thr  Val  Pro  Ala  Ile  Ser  Pro  Val  Gln  Thr  Pro  Leu
145                      150                      155                      160

Thr  Ser  Pro  Pro  Ala  Pro  Pro  Thr  Glu  Ala  Pro  Ala  Pro  Thr  Leu  Gly
               165                      170                      175

Ala  Ala  Thr  Pro  Gly  Pro  Ala  Gly  Thr  Asp  Thr  Ser  Gly  Ala  Asn  Gln
               180                      185                      190

Met  Trp  Thr  Val  Gln  Lys  Met  Met  Gly  Ser  Leu  Ala  Met  Gly  Trp  Ala
          195                      200                      205

Leu  Leu  Asn  Leu  Met  Val
     210
```

(2) INFORMATION FOR SEQ ID NO:5:

(i) SEQUENCE CHARACTERISTICS:
        (A) LENGTH: 2230 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Daucus carota (vii) IMMEDIATE SOURCE:
        (B) CLONE: extensin gene (ix) FEATURE:
        (A) NAME/KEY: CDS
        (B) LOCATION: 750..1670

(ix) FEATURE:
        (A) NAME/KEY: sig_peptide
        (B) LOCATION: 750..845

(xi) SEQUENCE DESCRIPTION: SEQ ID NO:5:

```
GAATTCATTA TTGACAGACT CAAAGTTAGA TTAGAGTACT AATTTGGCCT TGTTTATCTC    60

TGATATAAAA CCGGTTACTA AATGAACTAA TTAAGTGATA CGCTAAGCAT GCCCTATGCC   120

CTATGTATCG ATTTTTATAA TTGATTTTTT TTTATTTGAC GTAATAGAAA TTTTAGGTTA   180

GAACTAAAAA GGTCAATACG AATAAACAAA ACTAGAAAAG GGAAATAAT TATTAATTTT    240

TTCTAGAATC GTATGTTAAA AATCTCCACA CACTTCATGT GTTATATATC GTGTGTGTGA   300

ATGCAGTAGC AAAACATTAC TAGATAGTTC AATTAGCTTG CAGGCCACTG AAAAAAAAAC   360

ACAATTAGAA ACACCGACTC TGAAAAGTAA AAATTATACA ATGAAAATAC GACAAGTCAT   420

TTGACATTTC AAACGAATGA TGTTAATATC ATGATCCAAA TTCTCATTCT TTTTTCTTTC   480

TTTCTTTTGA CAGAGATCCA AATTCTCATT CTGATAATAC ATGTTTAGAT ATAGTTGTTG   540
```

-continued

```
ACTTGTTGGC CTCTGCAGAG GGAAAAAAGA AAGAAAAAAA AATAAAGAAA GAGAGTTGTT    600

GGCTTCTTCA AATATTTATA TATATTTAAG TAACATTTTG TACCGATTAT TGAAATCATC    660

TGTCACGGTG AGTAGATCAC CAAGGCTATA AATAGAGGGC CAGTTTTAGT TGAAAGCATA    720

ACACAACAAG CCTTTTGGTT GTAGTAAAC ATG GGA AGA ATT GCT AGA GGC TCA     773
                                Met Gly Arg Ile Ala Arg Gly Ser
                                 1               5

AAA ATG AGT TCT CTC ATT GTG TCT TTG CTT GTA GTA TTG GTG TCA CTC      821
Lys Met Ser Ser Leu Ile Val Ser Leu Leu Val Val Leu Val Ser Leu
    10              15                  20

AAT TTG GCT TCC GAA ACC ACA GCT AAA TAC ACT TAC TCC TCT CCA CCA      869
Asn Leu Ala Ser Glu Thr Thr Ala Lys Tyr Thr Tyr Ser Ser Pro Pro
25              30                  35                  40

CCT CCC GAG CAT TCT CCT CCA CCG CCG GAG CAT TCT CCT CCT CCG CCT      917
Pro Pro Glu His Ser Pro Pro Pro Pro Glu His Ser Pro Pro Pro Pro
                    45                  50                  55

TAC CAC TAC GAA TCC CCG CCC CCG CCT AAA CAT TCT CCA CCA CCA CCT      965
Tyr His Tyr Glu Ser Pro Pro Pro Pro Lys His Ser Pro Pro Pro Pro
                60                  65                  70

ACA CCG GTT TAC AAG TAC AAG TCT CCA CCG CCT CCT ATG CAT TCT CCT     1013
Thr Pro Val Tyr Lys Tyr Lys Ser Pro Pro Pro Pro Met His Ser Pro
        75                  80                  85

CCA CCG CCT TAT CAT TTT GAG TCT CCA CCT CCA CCA AAA CAT TCT CCA     1061
Pro Pro Pro Tyr His Phe Glu Ser Pro Pro Pro Pro Lys His Ser Pro
        90                  95                  100

CCA CCA CCA ACG CCG GTT TAC AAG TAC AAA TCT CCA CCA CCA CCT AAA     1109
Pro Pro Pro Thr Pro Val Tyr Lys Tyr Lys Ser Pro Pro Pro Pro Lys
105             110                 115                 120

CAT TCT CCT GCA CCA GTG CAT CAT TAT AAA TAC AAG TCT CCA CCA CCA     1157
His Ser Pro Ala Pro Val His His Tyr Lys Tyr Lys Ser Pro Pro Pro
            125                 130                 135

CCA ACA CCG GTT TAT AAG TAT AAA TCT CCA CCA CCA AAG CAT TCT         1205
Pro Thr Pro Val Tyr Lys Tyr Lys Ser Pro Pro Pro Lys His Ser
        140                 145                 150

CCT GCA CCA GAA CAT CAC TAT AAG TAC AAG TCT CCA CCA CCA CCT AAG     1253
Pro Ala Pro Glu His His Tyr Lys Tyr Lys Ser Pro Pro Pro Pro Lys
        155                 160                 165

CAT TTT CCT GCA CCA GAA CAT CAC TAT AAG TAC AAG TAC AAG TCT CCA     1301
His Phe Pro Ala Pro Glu His His Tyr Lys Tyr Lys Tyr Lys Ser Pro
170                 175                 180

CCA CCA CCA ACA CCG GTC TAC AAG TAT AAA TCT CCA CCA CCT CCA ACA     1349
Pro Pro Pro Thr Pro Val Tyr Lys Tyr Lys Ser Pro Pro Pro Pro Thr
185                 190                 195                 200

CCG GTC TAC AAG TAC AAG TCT CCA CCA CCC AAG CAT TCT CCC GCA         1397
Pro Val Tyr Lys Tyr Lys Ser Pro Pro Pro Lys His Ser Pro Ala
            205                 210                 215

CCA GTA CAC CAT TAC AAG TAC AAG TCT CCA CCA CCA ACT CCA GTT         1445
Pro Val His His Tyr Lys Tyr Lys Ser Pro Pro Pro Thr Pro Val
        220                 225                 230

TAT AAA TCT CCA CCA CCA CCC GAA CAT TCC CCA CCA CCA ACA CCG         1493
Tyr Lys Ser Pro Pro Pro Pro Glu His Ser Pro Pro Pro Thr Pro
        235                 240                 245

GTC TAC AAA TAC AAG TCT CCA CCA CCA CCA ATG CAC TCT CCA CCA CCA     1541
Val Tyr Lys Tyr Lys Ser Pro Pro Pro Pro Met His Ser Pro Pro Pro
        250                 255                 260

CCA ACA CCA GTT TAC AAG TAC AAG TCT CCG CCA CCA CCA ATG CAC TCT     1589
Pro Thr Pro Val Tyr Lys Tyr Lys Ser Pro Pro Pro Pro Met His Ser
265                 270                 275                 280
```

| | | | | | | | | | | | | | | | |
|---|---|---|---|---|---|---|---|---|---|---|---|---|---|---|---|
| CCC | CCA | CCA | CCA | GTT | TAC | TCT | CCA | CCA | CCA | CCC | AAA | CAT | CAC | TAC | TCC |
| Pro | Pro | Pro | Pro | Val 285 | Tyr | Ser | Pro | Pro 290 | Pro | Pro | Lys | His | His | Tyr 295 | Ser |

1637

| | | | | | | | | | |
|---|---|---|---|---|---|---|---|---|---|
| TAT | ACG | TCA | CCT | CCT | CCT | CCT | CAC | CAC | TAC TAATAAAAAC TCTCCCTAAA |
| Tyr | Thr | Ser | Pro 300 | Pro | Pro | Pro | His | His 305 | Tyr |

1687

```
GGTACGTGTT AATCTTAATG CATGGGTCAT GAAAATGTAT AATGAACTAA AATTAAAGTT    1747
AACATCTAAT AATATCTATA CCTATTTAAC GTAAGACATT TTATGTTTCT TTATAGAATC    1807
TTTTGTGGAA AAATGTAACT ATATAAATTG GAATGGCCAT TTACTAAAGT TCATATACAT    1867
TTCGAGGACA CTGATGGAGG CCAACTTAAG AAGATGAAGT AAAATAATGG CTTGCACGAT    1927
GATTTGGCG TTTTTATAAA TATGTTGATC GAATATGATA TTTTTGTTGT ATTCTAGTAT     1987
GGGTCATTTC GTTTTTCTTT GCGAATGAAT AACATTTACA TATGCATGTA GCATCGGGGA    2047
ACCTCTTGAC CTCTAGAAAT AGAGGTTTGT TATTGTGGCA TTAAAGCAAT TATATGAATA    2107
AGTATTTCTG TTATGAATTA ATGCCATTAC TAGCTAGTAG TATTATTTGT GAGGTCTGCG    2167
AGGATCGAAA CAGAAAGAGT ACTTGAGACA CTTATTGACA ATGAAAAAAA AATTAATTTA    2227
AAA                                                                 2230
```

( 2 ) INFORMATION FOR SEQ ID NO:6:

( i ) SEQUENCE CHARACTERISTICS:
      ( A ) LENGTH: 306 amino acids
      ( B ) TYPE: amino acid
      ( D ) TOPOLOGY: linear ( i i ) MOLECULE TYPE: protein ( x i ) SEQUENCE DESCRIPTION: SEQ ID NO:6:

| | | | | | | | | | | | | | | | |
|---|---|---|---|---|---|---|---|---|---|---|---|---|---|---|---|
| Met 1 | Gly | Arg | Ile | Ala 5 | Arg | Gly | Ser | Lys | Met 10 | Ser | Ser | Leu | Ile | Val 15 | Ser |
| Leu | Leu | Val | Val 20 | Leu | Val | Ser | Leu | Asn 25 | Leu | Ala | Ser | Glu | Thr 30 | Thr | Ala |
| Lys | Tyr | Thr 35 | Tyr | Ser | Ser | Pro | Pro 40 | Pro | Pro | Glu | His | Ser 45 | Pro | Pro | Pro |
| Pro | Glu 50 | His | Ser | Pro | Pro | Pro 55 | Pro | Tyr | His | Tyr | Glu 60 | Ser | Pro | Pro | Pro |
| Pro 65 | Lys | His | Ser | Pro | Pro 70 | Pro | Pro | Thr | Pro | Val 75 | Tyr | Lys | Tyr | Lys | Ser 80 |
| Pro | Pro | Pro | Pro | Met 85 | His | Ser | Pro | Pro | Pro 90 | Pro | Tyr | His | Phe | Glu 95 | Ser |
| Pro | Pro | Pro | Pro 100 | Lys | His | Ser | Pro | Pro 105 | Pro | Pro | Thr | Pro | Val 110 | Tyr | Lys |
| Tyr | Lys | Ser 115 | Pro | Pro | Pro | Pro | Lys 120 | His | Ser | Pro | Ala | Pro 125 | Val | His | His |
| Tyr | Lys 130 | Tyr | Lys | Ser | Pro | Pro 135 | Pro | Pro | Thr | Pro | Val 140 | Tyr | Lys | Tyr | Lys |
| Ser 145 | Pro | Pro | Pro | Pro | Lys 150 | His | Ser | Pro | Ala | Pro 155 | Glu | His | His | Tyr | Lys 160 |
| Tyr | Lys | Ser | Pro | Pro 165 | Pro | Pro | Lys | His | Phe 170 | Pro | Ala | Pro | Glu | His 175 | His |
| Tyr | Lys | Tyr | Lys 180 | Tyr | Lys | Ser | Pro | Pro 185 | Pro | Pro | Thr | Pro | Val 190 | Tyr | Lys |
| Tyr | Lys | Ser 195 | Pro | Pro | Pro | Pro | Thr 200 | Pro | Val | Tyr | Lys | Tyr 205 | Lys | Ser | Pro |

-continued

```
Pro  Pro  Pro  Lys  His  Ser  Pro  Ala  Pro  Val  His  His  Tyr  Lys  Tyr  Lys
     210                 215                      220
Ser  Pro  Pro  Pro  Pro  Thr  Pro  Val  Tyr  Lys  Ser  Pro  Pro  Pro  Pro  Glu
225                      230                 235                           240
His  Ser  Pro  Pro  Pro  Pro  Thr  Pro  Val  Tyr  Lys  Tyr  Lys  Ser  Pro  Pro
               245                      250                           255
Pro  Pro  Met  His  Ser  Pro  Pro  Pro  Pro  Thr  Pro  Val  Tyr  Lys  Tyr  Lys
               260                      265                      270
Ser  Pro  Pro  Pro  Pro  Met  His  Ser  Pro  Pro  Pro  Pro  Val  Tyr  Ser  Pro
          275                      280                      285
Pro  Pro  Pro  Lys  His  His  Tyr  Ser  Tyr  Thr  Ser  Pro  Pro  Pro  Pro  His
          290                 295                      300
His  Tyr
305
```

( 2 ) INFORMATION FOR SEQ ID NO:7:

( i ) SEQUENCE CHARACTERISTICS:
        ( A ) LENGTH: 2077 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i i ) IMMEDIATE SOURCE:
        ( B ) CLONE: xylanase gene XYNB ( i x ) FEATURE:
        ( A ) NAME/KEY: CDS
        ( B ) LOCATION: 299..2077

( i x ) FEATURE:
        ( A ) NAME/KEY: misc_feature
        ( B ) LOCATION: 299..632
        ( D ) OTHER INFORMATION: /function="cellulose binding
            domain"

( x i ) SEQUENCE DESCRIPTION: SEQ ID NO:7:

```
GGATCCCCGG  GTACCGAGCT  CGAATTCGGA  TTCCAGGGGA  CAAAAAATAA  TAATGCGGCC    60

CAGGCTCCGG  CAGTGACAGG  AAGTATTTGC  CGATAAAAAA  TTTTCCAACA  GCACTTCAGA   120

ATAAGAAATC  ACAGCGGTAG  TTAACGCACT  GTGAAATACA  TCAACCAAAC  TCATGCTGCA   180

TCAGTACTCA  TGTGCAAGCT  GTCGATTGTA  CCCCGTACTG  AATTAACCCG  GTCTTCGGAC   240

CGGGTATTTT  TACAAGCAGC  ACCCGCAATT  CATCCCTATA  AATTCCATGG  AGATTACC    298

ATG  ACA  ATT  TCC  GCA  AGC  GAT  TAC  CGT  CAC  CCG  GGT  AAT  TTT  TTA  AAA   346
Met  Thr  Ile  Ser  Ala  Ser  Asp  Tyr  Arg  His  Pro  Gly  Asn  Phe  Leu  Lys
  1                   5                        10                      15

CGT  ACA  ACA  GCG  CTA  TTG  TGC  GTC  GGC  ACT  GCA  CTA  ACA  GCC  CTG  GCC   394
Arg  Thr  Thr  Ala  Leu  Leu  Cys  Val  Gly  Thr  Ala  Leu  Thr  Ala  Leu  Ala
                    20                      25                      30

TTT  AAC  GCA  TCG  GCT  GCC  TGT  ACC  TAC  ACC  ATC  GAT  AGC  GAA  TGG  TCC   442
Phe  Asn  Ala  Ser  Ala  Ala  Cys  Thr  Tyr  Thr  Ile  Asp  Ser  Glu  Trp  Ser
               35                      40                      45

ACC  GGC  TTT  ACC  GCC  AAT  ATC  ACC  CTC  AAA  AAC  GAT  ACC  GGT  GCC  GCC   490
Thr  Gly  Phe  Thr  Ala  Asn  Ile  Thr  Leu  Lys  Asn  Asp  Thr  Gly  Ala  Ala
          50                      55                      60

ATC  AAT  AAC  TGG  AAC  GTG  AAT  TGG  CAA  TAC  TCC  AGC  AAT  CGC  ATG  ACC   538
Ile  Asn  Asn  Trp  Asn  Val  Asn  Trp  Gln  Tyr  Ser  Ser  Asn  Arg  Met  Thr
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| 65  |     |     |     |     |     | 70  |     |     |     |     | 75  |     |     |     | 80  |      |
| AGC | GGC | TGG | AAT | GCC | AAC | TTC | TCC | GGC | ACC | AAC | CCC | TAC | AAC | GCC | ACC | 586  |
| Ser | Gly | Trp | Asn | Ala | Asn | Phe | Ser | Gly | Thr | Asn | Pro | Tyr | Asn | Ala | Thr |      |
|     |     |     |     |  85 |     |     |     |     |  90 |     |     |     |     |  95 |     |      |
| AAC | ATG | AGC | TGG | AAC | GGC | AGC | ATC | GCG | CCA | GGA | CAA | TCC | ATC | TCC | TTC | 634  |
| Asn | Met | Ser | Trp | Asn | Gly | Ser | Ile | Ala | Pro | Gly | Gln | Ser | Ile | Ser | Phe |      |
|     |     |     | 100 |     |     |     |     | 105 |     |     |     |     | 110 |     |     |      |
| GGC | CTC | CAG | GGC | GAA | AAA | AAT | GGC | AGC | ACC | GCC | GAG | CGA | CCA | ACC | GTC | 682  |
| Gly | Leu | Gln | Gly | Glu | Lys | Asn | Gly | Ser | Thr | Ala | Glu | Arg | Pro | Thr | Val |      |
|     |     | 115 |     |     |     |     | 120 |     |     |     |     | 125 |     |     |     |      |
| ACC | GGC | GCC | GCT | TGT | AAC | AGT | GCA | ACC | ACC | AGC | TCT | GTG | GCT | TCC | AGC | 730  |
| Thr | Gly | Ala | Ala | Cys | Asn | Ser | Ala | Thr | Thr | Ser | Ser | Val | Ala | Ser | Ser |      |
|     | 130 |     |     |     |     | 135 |     |     |     |     | 140 |     |     |     |     |      |
| TCT | TCA | ACA | CCC | ACC | ACC | AGT | TCA | TCT | TCT | GCA | TCC | AGT | GTG | GCC | TCC | 778  |
| Ser | Ser | Thr | Pro | Thr | Thr | Ser | Ser | Ser | Ser | Ala | Ser | Ser | Val | Ala | Ser |      |
| 145 |     |     |     |     | 150 |     |     |     |     | 155 |     |     |     |     | 160 |      |
| GCA | CTG | CTG | TTG | CAA | GAA | GCA | CAA | GCC | GGT | TTC | TGC | CGT | GTG | GAT | GGC | 826  |
| Ala | Leu | Leu | Leu | Gln | Glu | Ala | Gln | Ala | Gly | Phe | Cys | Arg | Val | Asp | Gly |      |
|     |     |     |     | 165 |     |     |     |     | 170 |     |     |     |     | 175 |     |      |
| ACC | ATC | GAT | AAT | AAC | CAC | ACC | GGC | TTT | ACC | GGC | AGT | GGC | TTT | GCC | AAC | 874  |
| Thr | Ile | Asp | Asn | Asn | His | Thr | Gly | Phe | Thr | Gly | Ser | Gly | Phe | Ala | Asn |      |
|     |     |     | 180 |     |     |     |     | 185 |     |     |     |     | 190 |     |     |      |
| ACC | AAC | AAT | GCC | CAG | GGG | GCA | GCG | GTA | GTC | TGG | GCG | ATA | GAT | GCT | ACC | 922  |
| Thr | Asn | Asn | Ala | Gln | Gly | Ala | Ala | Val | Val | Trp | Ala | Ile | Asp | Ala | Thr |      |
|     |     | 195 |     |     |     |     | 200 |     |     |     |     | 205 |     |     |     |      |
| AGC | AGT | GGC | CGT | CGC | ACC | CTG | ACT | ATC | CGC | TAT | GCC | AAT | GGT | GGA | ACC | 970  |
| Ser | Ser | Gly | Arg | Arg | Thr | Leu | Thr | Ile | Arg | Tyr | Ala | Asn | Gly | Gly | Thr |      |
|     | 210 |     |     |     |     | 215 |     |     |     |     | 220 |     |     |     |     |      |
| GCC | AAT | CGC | AAT | GGC | TCA | CTG | GTG | ATT | AAC | GGC | GGC | AGC | AAC | GGT | AAC | 1018 |
| Ala | Asn | Arg | Asn | Gly | Ser | Leu | Val | Ile | Asn | Gly | Gly | Ser | Asn | Gly | Asn |      |
| 225 |     |     |     |     | 230 |     |     |     |     | 235 |     |     |     |     | 240 |      |
| TAT | ACG | GTG | AGT | TTG | CCC | ACG | ACC | GGC | GCC | TGG | ACC | ACC | TGG | CAA | ACC | 1066 |
| Tyr | Thr | Val | Ser | Leu | Pro | Thr | Thr | Gly | Ala | Trp | Thr | Thr | Trp | Gln | Thr |      |
|     |     |     |     | 245 |     |     |     |     | 250 |     |     |     |     | 255 |     |      |
| GCA | ACT | ATC | GAT | GTG | GAT | TTG | GTA | CAG | GGC | AAT | AAT | ATT | GTG | CAG | TTG | 1114 |
| Ala | Thr | Ile | Asp | Val | Asp | Leu | Val | Gln | Gly | Asn | Asn | Ile | Val | Gln | Leu |      |
|     |     |     | 260 |     |     |     |     | 265 |     |     |     |     | 270 |     |     |      |
| TCT | GCA | ACG | ACA | GCC | GAA | GGC | TTA | CCC | AAT | ATA | GAT | TCG | TTA | AGT | GTT | 1162 |
| Ser | Ala | Thr | Thr | Ala | Glu | Gly | Leu | Pro | Asn | Ile | Asp | Ser | Leu | Ser | Val |      |
|     |     | 275 |     |     |     |     | 280 |     |     |     |     | 285 |     |     |     |      |
| GTG | GGT | GGT | ACG | GTC | AGG | GCG | GGT | AAT | TGC | GGC | AGT | GTG | AGC | AGC | AGC | 1210 |
| Val | Gly | Gly | Thr | Val | Arg | Ala | Gly | Asn | Cys | Gly | Ser | Val | Ser | Ser | Ser |      |
|     | 290 |     |     |     |     | 295 |     |     |     |     | 300 |     |     |     |     |      |
| AGT | TCC | GTG | CAA | TCG | TCA | TCA | TCG | AGC | AGT | AGC | TCA | AGT | GCT | GCA | TCG | 1258 |
| Ser | Ser | Val | Gln | Ser | Ser | Ser | Ser | Ser | Ser | Ser | Ser | Ser | Ala | Ala | Ser |      |
| 305 |     |     |     |     | 310 |     |     |     |     | 315 |     |     |     |     | 320 |      |
| GCC | AAA | AAA | TTT | ATT | GGC | AAC | ATT | ACA | ACG | TCC | GGC | GCC | GTG | AGA | TCC | 1306 |
| Ala | Lys | Lys | Phe | Ile | Gly | Asn | Ile | Thr | Thr | Ser | Gly | Ala | Val | Arg | Ser |      |
|     |     |     |     | 325 |     |     |     |     | 330 |     |     |     |     | 335 |     |      |
| GAC | TTC | ACC | CGC | TAT | TGG | AAT | CAG | ATT | ACT | CCT | GAA | AAT | GAA | AGC | AAG | 1354 |
| Asp | Phe | Thr | Arg | Tyr | Trp | Asn | Gln | Ile | Thr | Pro | Glu | Asn | Glu | Ser | Lys |      |
|     |     |     | 340 |     |     |     |     | 345 |     |     |     |     | 350 |     |     |      |
| TGG | GGT | TCG | GTT | GAA | GGC | ACT | CGT | AAC | GTT | TAC | AAC | TGG | GCG | CCA | TTG | 1402 |
| Trp | Gly | Ser | Val | Glu | Gly | Thr | Arg | Asn | Val | Tyr | Asn | Trp | Ala | Pro | Leu |      |
|     |     | 355 |     |     |     |     | 360 |     |     |     |     | 365 |     |     |     |      |
| GAT | CGC | ATC | TAT | GCC | TAT | GCC | CGC | CAG | AAT | AAT | ATT | CCG | GTA | AAA | GCC | 1450 |
| Asp | Arg | Ile | Tyr | Ala | Tyr | Ala | Arg | Gln | Asn | Asn | Ile | Pro | Val | Lys | Ala |      |
|     | 370 |     |     |     |     | 375 |     |     |     |     | 380 |     |     |     |     |      |
| CAC | ACC | TTT | GTG | TGG | GGT | GCA | CAA | TCA | CCT | TCA | TGG | CTG | AAC | AAT | TTG | 1498 |

|     |     |     |     |     |     |     |     |     |     |     |     |     |     |     |      |
|-----|-----|-----|-----|-----|-----|-----|-----|-----|-----|-----|-----|-----|-----|-----|------|
| His | Thr | Phe | Val | Trp | Gly | Ala | Gln | Ser | Pro | Ser | Trp | Leu | Asn | Asn | Leu  |
| 385 |     |     |     |     | 390 |     |     |     | 395 |     |     |     |     |     | 400  |
| AGC | GGC | CCG | GAA | GTT | GCC | GTT | GAA | ATT | GAG | CAG | TGG | ATT | CGC | GAT | TAC  | 1546 |
| Ser | Gly | Pro | Glu | Val | Ala | Val | Glu | Ile | Glu | Gln | Trp | Ile | Arg | Asp | Tyr  |
|     |     |     |     | 405 |     |     |     |     | 410 |     |     |     |     | 415 |      |
| TGT | GCG | CGC | TAC | CCG | GAT | ACC | GCC | ATG | ATC | GAC | GTG | GTG | AAC | GAA | GCG  | 1594 |
| Cys | Ala | Arg | Tyr | Pro | Asp | Thr | Ala | Met | Ile | Asp | Val | Val | Asn | Glu | Ala  |
|     |     |     | 420 |     |     |     |     | 425 |     |     |     |     | 430 |     |      |
| GTG | CCA | GGC | CAC | CAG | CCT | GCA | GGT | TAT | GCG | CAA | AGG | GCT | TTT | GGC | AAT  | 1642 |
| Val | Pro | Gly | His | Gln | Pro | Ala | Gly | Tyr | Ala | Gln | Arg | Ala | Phe | Gly | Asn  |
|     |     | 435 |     |     |     |     | 440 |     |     |     |     | 445 |     |     |      |
| AAC | TGG | ATC | CAG | CGC | GTT | TTC | CAA | CTG | GCG | CGC | CAA | TAT | TGC | CCC | AAC  | 1690 |
| Asn | Trp | Ile | Gln | Arg | Val | Phe | Gln | Leu | Ala | Arg | Gln | Tyr | Cys | Pro | Asn  |
|     | 450 |     |     |     |     | 455 |     |     |     |     | 460 |     |     |     |      |
| TCC | ATT | TTG | ATC | CTG | AAC | GAC | TAC | AAC | AAT | ATT | CGC | TGG | CAG | CAC | AAC  | 1738 |
| Ser | Ile | Leu | Ile | Leu | Asn | Asp | Tyr | Asn | Asn | Ile | Arg | Trp | Gln | His | Asn  |
| 465 |     |     |     |     | 470 |     |     |     |     | 475 |     |     |     |     | 480  |
| GAG | TTT | ATC | GCG | CTC | GCT | AAA | GCC | CAA | GGC | AAT | TAT | ATT | GAT | GCA | GTC  | 1786 |
| Glu | Phe | Ile | Ala | Leu | Ala | Lys | Ala | Gln | Gly | Asn | Tyr | Ile | Asp | Ala | Val  |
|     |     |     |     | 485 |     |     |     |     | 490 |     |     |     |     | 495 |      |
| GGT | CTG | CAG | GCT | CAC | GAA | TTG | AAA | GGC | ATG | ACC | GCA | GCG | CAA | GTT | AAA  | 1834 |
| Gly | Leu | Gln | Ala | His | Glu | Leu | Lys | Gly | Met | Thr | Ala | Ala | Gln | Val | Lys  |
|     |     |     |     | 500 |     |     |     |     | 505 |     |     |     |     | 510 |      |
| ACC | GCC | ATC | GAC | AAT | ATT | TGG | AAC | CAG | GTG | GGC | AAG | CCC | ATT | TAC | ATT  | 1882 |
| Thr | Ala | Ile | Asp | Asn | Ile | Trp | Asn | Gln | Val | Gly | Lys | Pro | Ile | Tyr | Ile  |
|     |     |     | 515 |     |     |     |     | 520 |     |     |     |     | 525 |     |      |
| TCC | GAA | TAC | GAC | ATT | GGT | GAC | ACC | AAT | GAC | CAG | GTT | CAA | TTG | CAG | AAC  | 1930 |
| Ser | Glu | Tyr | Asp | Ile | Gly | Asp | Thr | Asn | Asp | Gln | Val | Gln | Leu | Gln | Asn  |
|     | 530 |     |     |     |     | 535 |     |     |     |     | 540 |     |     |     |      |
| TTC | CAG | GCT | CAC | TTC | CCC | GTG | TTC | TAC | AAC | CAT | CCA | CAT | GTG | CAT | GGC  | 1978 |
| Phe | Gln | Ala | His | Phe | Pro | Val | Phe | Tyr | Asn | His | Pro | His | Val | His | Gly  |
| 545 |     |     |     |     | 550 |     |     |     |     | 555 |     |     |     |     | 560  |
| ATT | ACC | TCT | GGG | ATA | TGT | GGT | GGG | CAG | GAC | CTG | GAT | CGA | AGG | CTC | CGG  | 2026 |
| Ile | Thr | Ser | Gly | Ile | Cys | Gly | Gly | Gln | Asp | Leu | Asp | Arg | Arg | Leu | Arg  |
|     |     |     |     | 565 |     |     |     |     | 570 |     |     |     |     | 575 |      |
| TTT | GAT | CCA | GGA | CAA | TGG | CAC | ACC | GCG | CCC | GGC | AAT | GAC | GTG | GTT | GAT  | 2074 |
| Phe | Asp | Pro | Gly | Gln | Trp | His | Thr | Ala | Pro | Gly | Asn | Asp | Val | Val | Asp  |
|     |     | 580 |     |     |     |     | 585 |     |     |     |     | 590 |     |     |      |
| TAA |     |     |     |     |     |     |     |     |     |     |     |     |     |     |      | 2077 |

( 2 ) INFORMATION FOR SEQ ID NO:8:

( i ) SEQUENCE CHARACTERISTICS:
        ( A ) LENGTH: 592 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

|     |     |     |     |     |     |     |     |     |     |     |     |     |     |     |
|-----|-----|-----|-----|-----|-----|-----|-----|-----|-----|-----|-----|-----|-----|-----|
| Met | Thr | Ile | Ser | Ala | Ser | Asp | Tyr | Arg | His | Pro | Gly | Asn | Phe | Leu | Lys |
| 1   |     |     |     | 5   |     |     |     |     | 10  |     |     |     |     | 15  |
| Arg | Thr | Thr | Ala | Leu | Leu | Cys | Val | Gly | Thr | Ala | Leu | Thr | Ala | Leu | Ala |
|     |     |     | 20  |     |     |     |     | 25  |     |     |     |     | 30  |     |
| Phe | Asn | Ala | Ser | Ala | Ala | Cys | Thr | Tyr | Thr | Ile | Asp | Ser | Glu | Trp | Ser |
|     |     | 35  |     |     |     |     | 40  |     |     |     |     | 45  |     |     |
| Thr | Gly | Phe | Thr | Ala | Asn | Ile | Thr | Leu | Lys | Asn | Asp | Thr | Gly | Ala | Ala |
|     | 50  |     |     |     |     | 55  |     |     |     |     | 60  |     |     |     |
| Ile | Asn | Asn | Trp | Asn | Val | Asn | Trp | Gln | Tyr | Ser | Ser | Asn | Arg | Met | Thr |
| 65  |     |     |     | 70  |     |     |     |     | 75  |     |     |     |     | 80  |

```
Ser Gly Trp Asn Ala Asn Phe Ser Gly Thr Asn Pro Tyr Asn Ala Thr
            85                      90                      95

Asn Met Ser Trp Asn Gly Ser Ile Ala Pro Gly Gln Ser Ile Ser Phe
            100                     105                     110

Gly Leu Gln Gly Glu Lys Asn Gly Ser Thr Ala Glu Arg Pro Thr Val
            115                     120                     125

Thr Gly Ala Ala Cys Asn Ser Ala Thr Thr Ser Ser Val Ala Ser Ser
        130                     135                     140

Ser Ser Thr Pro Thr Thr Ser Ser Ser Ala Ser Ser Val Ala Ser
145                     150                     155                 160

Ala Leu Leu Leu Gln Glu Ala Gln Ala Gly Phe Cys Arg Val Asp Gly
                165                     170                     175

Thr Ile Asp Asn Asn His Thr Gly Phe Thr Gly Ser Gly Phe Ala Asn
            180                     185                     190

Thr Asn Asn Ala Gln Gly Ala Ala Val Val Trp Ala Ile Asp Ala Thr
            195                     200                     205

Ser Ser Gly Arg Arg Thr Leu Thr Ile Arg Tyr Ala Asn Gly Gly Thr
    210                     215                     220

Ala Asn Arg Asn Gly Ser Leu Val Ile Asn Gly Gly Ser Asn Gly Asn
225                     230                     235                 240

Tyr Thr Val Ser Leu Pro Thr Thr Gly Ala Trp Thr Thr Trp Gln Thr
                245                     250                     255

Ala Thr Ile Asp Val Asp Leu Val Gln Gly Asn Asn Ile Val Gln Leu
            260                     265                     270

Ser Ala Thr Thr Ala Glu Gly Leu Pro Asn Ile Asp Ser Leu Ser Val
    275                     280                     285

Val Gly Gly Thr Val Arg Ala Gly Asn Cys Gly Ser Val Ser Ser Ser
    290                     295                     300

Ser Ser Val Gln Ser Ser Ser Ser Ser Ser Ser Ser Ala Ala Ser
305                     310                     315                 320

Ala Lys Lys Phe Ile Gly Asn Ile Thr Thr Ser Gly Ala Val Arg Ser
            325                     330                     335

Asp Phe Thr Arg Tyr Trp Asn Gln Ile Thr Pro Glu Asn Glu Ser Lys
            340                     345                     350

Trp Gly Ser Val Glu Gly Thr Arg Asn Val Tyr Asn Trp Ala Pro Leu
        355                     360                     365

Asp Arg Ile Tyr Ala Tyr Ala Arg Gln Asn Asn Ile Pro Val Lys Ala
    370                     375                     380

His Thr Phe Val Trp Gly Ala Gln Ser Pro Ser Trp Leu Asn Asn Leu
385                     390                     395                 400

Ser Gly Pro Glu Val Ala Val Glu Ile Glu Gln Trp Ile Arg Asp Tyr
            405                     410                     415

Cys Ala Arg Tyr Pro Asp Thr Ala Met Ile Asp Val Val Asn Glu Ala
            420                     425                     430

Val Pro Gly His Gln Pro Ala Gly Tyr Ala Gln Arg Ala Phe Gly Asn
        435                     440                     445

Asn Trp Ile Gln Arg Val Phe Gln Leu Ala Arg Gln Tyr Cys Pro Asn
    450                     455                     460

Ser Ile Leu Ile Leu Asn Asp Tyr Asn Asn Ile Arg Trp Gln His Asn
465                     470                     475                 480

Glu Phe Ile Ala Leu Ala Lys Ala Gln Gly Asn Tyr Ile Asp Ala Val
            485                     490                     495
```

```
Gly  Leu  Gln  Ala  His  Glu  Leu  Lys  Gly  Met  Thr  Ala  Ala  Gln  Val  Lys
               500                      505                 510

Thr  Ala  Ile  Asp  Asn  Ile  Trp  Asn  Gln  Val  Gly  Lys  Pro  Ile  Tyr  Ile
          515                      520                      525

Ser  Glu  Tyr  Asp  Ile  Gly  Asp  Thr  Asn  Asp  Gln  Val  Gln  Leu  Gln  Asn
     530                      535                 540

Phe  Gln  Ala  His  Phe  Pro  Val  Phe  Tyr  Asn  His  Pro  His  Val  His  Gly
545                      550                 555                           560

Ile  Thr  Ser  Gly  Ile  Cys  Gly  Gly  Gln  Asp  Leu  Asp  Arg  Arg  Leu  Arg
               565                      570                      575

Phe  Asp  Pro  Gly  Gln  Trp  His  Thr  Ala  Pro  Gly  Asn  Asp  Val  Val  Asp
               580                      585                 590
```

( 2 ) INFORMATION FOR SEQ ID NO:9:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( C ) INDIVIDUAL ISOLATE: MM175

( x i ) SEQUENCE DESCRIPTION: SEQ ID NO:9:

CATGGCTGGA T                    11

( 2 ) INFORMATION FOR SEQ ID NO:10:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( C ) INDIVIDUAL ISOLATE: MM176

( x i ) SEQUENCE DESCRIPTION: SEQ ID NO:10:

CGATCCAGC                    9

( 2 ) INFORMATION FOR SEQ ID NO:11:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( C ) INDIVIDUAL ISOLATE: MM170

( x i ) SEQUENCE DESCRIPTION: SEQ ID NO:11:

GCTATGTCAC CAACATCATG GACG           24

( 2 ) INFORMATION FOR SEQ ID NO:12:

( i ) SEQUENCE CHARACTERISTICS:
        ( A ) LENGTH: 30 base pairs
        ( B ) TYPE: nucleic acid
        ( C ) STRANDEDNESS: single ( D ) TOPOLOGY: linear ( i i ) MOLECULE TYPE: DNA (genomic)

( v i ) ORIGINAL SOURCE:
            ( C ) INDIVIDUAL ISOLATE: MM172

( x i ) SEQUENCE DESCRIPTION: SEQ ID NO:12:

CCGGATCCGA GATCTGACGC CCGCAAGGTC 30

( 2 ) INFORMATION FOR SEQ ID NO:13:

( i ) SEQUENCE CHARACTERISTICS:
            ( A ) LENGTH: 24 base pairs
            ( B ) TYPE: nucleic acid
            ( C ) STRANDEDNESS: single
            ( D ) TOPOLOGY: linear ( i i ) MOLECULE TYPE: DNA (genomic)

( v i ) ORIGINAL SOURCE:
            ( C ) INDIVIDUAL ISOLATE: MM143

( x i ) SEQUENCE DESCRIPTION: SEQ ID NO:13:

CGCGCCATGG GTCAAACGAG AAGG 24

( 2 ) INFORMATION FOR SEQ ID NO:14:

( i ) SEQUENCE CHARACTERISTICS:
            ( A ) LENGTH: 29 base pairs
            ( B ) TYPE: nucleic acid
            ( C ) STRANDEDNESS: single
            ( D ) TOPOLOGY: linear ( i i ) MOLECULE TYPE: DNA (genomic)

( v i ) ORIGINAL SOURCE:
            ( C ) INDIVIDUAL ISOLATE: MM144

( x i ) SEQUENCE DESCRIPTION: SEQ ID NO:14:

CGCGCTGCAG CGTCATGACG CCCGCAAGG 29

( 2 ) INFORMATION FOR SEQ ID NO:15:

( i ) SEQUENCE CHARACTERISTICS:
            ( A ) LENGTH: 37 base pairs
            ( B ) TYPE: nucleic acid
            ( C ) STRANDEDNESS: single
            ( D ) TOPOLOGY: linear ( i i ) MOLECULE TYPE: DNA (genomic)

( v i i ) IMMEDIATE SOURCE:
            ( B ) CLONE: MM148

( x i ) SEQUENCE DESCRIPTION: SEQ ID NO:15:

CCATGGGTCA AACGAGAAGG GTTGTGCTCA AGTCTGC 37

( 2 ) INFORMATION FOR SEQ ID NO:16:

( i ) SEQUENCE CHARACTERISTICS:
            ( A ) LENGTH: 45 base pairs
            ( B ) TYPE: nucleic acid
            ( C ) STRANDEDNESS: single
            ( D ) TOPOLOGY: linear ( i i ) MOLECULE TYPE: DNA (genomic)

( v i i ) IMMEDIATE SOURCE:
            ( B ) CLONE: MM149

( x i ) SEQUENCE DESCRIPTION: SEQ ID NO:16:

GGCCGCAGAC TTGAGCACAA CCCTTCTCGT TTGACCCATG GCATG    4 5